United States Patent
Romkina et al.

(10) Patent No.: US 10,392,638 B2
(45) Date of Patent: Aug. 27, 2019

(54) METHOD FOR PRODUCING L-AMINO ACIDS USING A BACTERIUM OF THE FAMILY ENTEROBACTERIACEAE OVEREXPRESSING A GENE ENCODING AN IRON EXPORTER

(71) Applicant: AJINOMOTO CO., INC., Tokyo (JP)

(72) Inventors: Anastasia Yurievna Romkina, Moscow (RU); Alexey Nikolaevich Chernyshov, Moscow (RU); Yulia Georgievna Rostova, Moscow (RU); Elvira Borisovna Voroshilova, Moscow (RU); Mikhail Yurievich Kiryukhin, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/106,830

(22) Filed: Aug. 21, 2018

(65) Prior Publication Data

US 2018/0355388 A1    Dec. 13, 2018

Related U.S. Application Data

(63) Continuation of application No. PCT/JP2017/007035, filed on Feb. 24, 2017.

(30) Foreign Application Priority Data

Feb. 25, 2016 (RU) ................. 2016106614

(51) Int. Cl.
| | |
|---|---|
| *C12P 13/04* | (2006.01) |
| *C12P 13/08* | (2006.01) |
| *C12P 13/06* | (2006.01) |
| *C12P 13/10* | (2006.01) |
| *C12P 13/12* | (2006.01) |
| *C12P 13/14* | (2006.01) |
| *C12P 13/24* | (2006.01) |
| *C07K 14/245* | (2006.01) |

(52) U.S. Cl.
CPC ............ *C12P 13/04* (2013.01); *C07K 14/245* (2013.01); *C12P 13/06* (2013.01); *C12P 13/08* (2013.01); *C12P 13/10* (2013.01); *C12P 13/12* (2013.01); *C12P 13/14* (2013.01); *C12P 13/24* (2013.01)

(58) Field of Classification Search
CPC ........... C12P 13/04; C12P 13/10; C12P 13/24; C12P 13/14; C12P 13/06; C12P 13/08; C12P 13/12; C07K 14/245
See application file for complete search history.

(56) References Cited

U.S. PATENT DOCUMENTS

| | | |
|---|---|---|
| 4,278,765 A | 7/1981 | Debabov et al. |
| 4,346,170 A | 8/1982 | Sano et al. |
| 5,661,012 A | 8/1997 | Sano et al. |
| 5,965,391 A | 10/1999 | Reinscheid et al. |
| 6,040,160 A | 3/2000 | Kojima et al. |
| 2006/0216796 A1 | 9/2006 | Hashiguchi et al. |

FOREIGN PATENT DOCUMENTS

| | | |
|---|---|---|
| EP | 0685555 A1 | 12/1995 |
| EP | 1979486 B1 | 4/2013 |
| WO | WO95/16042 A1 | 6/1995 |
| WO | WO96/15246 A1 | 5/1996 |
| WO | WO2007/086618 A1 | 8/2007 |

OTHER PUBLICATIONS

Sousa et al., Microbiology 148(Pt5):1291-1303, 2002.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Nicolaou et al., Applied and Environmental Microbiology 79(23):7210-7219, published Sep. 13, 2013.*
Roberts et al., GenBank accession No. U82664, 1997.*
Grass et al., Arch Microbiol 183:9-18, published online Nov. 11, 2004.*
Plunkett et al., GenBank accession No. L19201, 1993.*
International Search Report for PCT Patent App. No. PCT/JP2017/007035 (dated May 22, 2017).
Written Opinion of the International Searching Authority for PCT Patent App. No. PCT/JP2017/007035 (dated May 22, 2017).
Sankari, S., et al., "A Bacterial Iron Exporter for Maintenance of Iron Homeostasis," J. Biol. Chem. 2014;289 (23):16498-16507.
Nicolaou, S. A., et al., "Overexpression of fetA (ybbL) and fetB (ybbM), Encoding an Iron Exporter, Enhances Resistance to Oxidative Stress in *Escherichia coil*," Appl. Environmen. Microbiol. 2013;79(23):7210-7219.
Grass, G., et al., "FieF (YiiP) from *Escherichia coli* mediates decreased cellular accumulation of iron and relieves iron stress," Arch. Microbiol. 2005;183:9-18.
Andrews, S. C., et al., "Bacterial iron homeostasis," FEMS Microbiol. Rev. 2003;27:215-237.
Köster, W., "ABC transporter-mediated uptake of iron, siderophores, heme and vitamin B12," Res. Microbiol. 2001;152:291-301.
Buchanan, S. K., et al., "Crystal structure of the outer membrane active transporter FepA from *Escherichia coli*," Nature Structural Biol. 1999;6(1):56-63.
Ferguson, A. D., et al., "Siderophore-Mediated Iron Transport: Crystal Structure of FhuA with Bound Lipopolysaccharide," Science 1998;282:2215-2220.
Ferguson, A. D., et al., "Structural Basis of Gating by the Outer Membrane Transporter FecA," Science 2002;295:1715-1719.

* cited by examiner

Primary Examiner — Delia M Ramirez
(74) Attorney, Agent, or Firm — Cermak Nakajima & McGowan LLP; Shelly Guest Cermak

(57) ABSTRACT

The present invention provides a method for producing L-amino acids by fermentation using a bacterium belonging to the family Enterobacteriaceae which has been modified to overexpress a gene encoding an iron exporter, such as a fetB gene, fetA gene, fieF gene, or a combination of these genes.

8 Claims, No Drawings

Specification includes a Sequence Listing.

SEQUENCE LISTING

<160> NUMBER OF SEQ ID NOS: 21

<210> SEQ ID NO 1
<211> LENGTH: 780
<212> TYPE: DNA
<213> ORGANISM: Escherichia coli

<400> SEQUENCE: 1
atgaactcgc ataatattac taacgaatca ttagcactgg cattaatgct ggtggtggtg      60
gcaatcttaa ttagccataa agaaaaactg gcgctggaga aagatattct ctggagcgtc     120
gggcgagcga taattcagct gattattgtc ggctatgtgc tgaagtatat tttcagcgtg     180

-continued

```
gatgatgcca gcctgacatt attgatggtg ttatttatct gctttaatgc ggcgtggaac      240
gcgcaaaaac gcagtaaata tattgctaaa gcttttatct catcgtttat tgccattacg      300 gtcgggcgg  gaattaccct ggcggtgctg attctctcag ggtcgattga atttatcccg      360
atgcaggtga tccctatcgc cgggatgatt gccggtaacg ccatggtagc ggtggggttg      420
tgttacaaca atttagggca acgggtcatt agcgaacagc aacagattca ggagaaactg      480
agtcttggtg cgacgccgaa gcaggcttca gcgatattga ttcgcgacag tattcgcgcg      540
gctttaattc cgacggtcga ttcagcaaaa acggttggct agtgagttt  accaggaatg      600 atgtccgggc tgatatttgc cgggattgat ccggtgaagg cgattaaata tcagattatg      660
gtgaccttta tgctgctctc aaccgccagc ttgtcgacca ttattgcctg ctatttaacc      720
tatcgtaagt tttataattc gcgccaccag ttggtggtga cgcaattgaa gaagaaatga      780
```

<210> SEQ ID NO 2
<211> LENGTH: 259
<212> TYPE: PRT
<213> ORGANISM: Escherichia coli

<400> SEQUENCE: 2

```
Met Asn Ser His Asn Ile Thr Asn Glu Ser Leu Ala Leu Ala Leu Met
1               5                   10                  15

Leu Val Val Ala Ile Leu Ile Ser His Lys Glu Lys Leu Ala Leu
            20                  25                  30

Glu Lys Asp Ile Leu Trp Ser Val Gly Arg Ala Ile Ile Gln Leu Ile
        35                  40                  45

Ile Val Gly Tyr Val Leu Lys Tyr Ile Phe Ser Val Asp Asp Ala Ser
    50                  55                  60

Leu Thr Leu Leu Met Val Leu Phe Ile Cys Phe Asn Ala Ala Trp Asn
65                  70                  75                  80

Ala Gln Lys Arg Ser Lys Tyr Ile Ala Lys Ala Phe Ile Ser Ser Phe
                85                  90                  95

Ile Ala Ile Thr Val Gly Ala Gly Ile Thr Leu Ala Val Leu Ile Leu
            100                 105                 110

Ser Gly Ser Ile Glu Phe Ile Pro Met Gln Val Ile Pro Ile Ala Gly
        115                 120                 125

Met Ile Ala Gly Asn Ala Met Val Ala Val Gly Leu Cys Tyr Asn Asn
    130                 135                 140

Leu Gly Gln Arg Val Ile Ser Glu Gln Gln Ile Gln Glu Lys Leu
145                 150                 155                 160

Ser Leu Gly Ala Thr Pro Lys Gln Ala Ser Ala Ile Leu Ile Arg Asp
                165                 170                 175

Ser Ile Arg Ala Ala Leu Ile Pro Thr Val Asp Ser Ala Lys Thr Val
            180                 185                 190

Gly Leu Val Ser Leu Pro Gly Met Met Ser Gly Leu Ile Phe Ala Gly
        195                 200                 205

Ile Asp Pro Val Lys Ala Ile Lys Tyr Gln Ile Met Val Thr Phe Met
    210                 215                 220

Leu Leu Ser Thr Ala Ser Leu Ser Thr Ile Ile Ala Cys Tyr Leu Thr
225                 230                 235                 240

Tyr Arg Lys Phe Tyr Asn Ser Arg His Gln Leu Val Val Thr Gln Leu
                245                 250                 255

Lys Lys Lys
```

```
<210> SEQ ID NO 3
<211> LENGTH: 678
<212> TYPE: DNA
<213> ORGANISM: Escherichia coli

<400> SEQUENCE: 3
atgcaggaaa atagtccttt gcttcagcta caaaacgtag gatatctggc gggtgatgcg      60
aagattctta ataacatcaa tttttcgctg cgtgctggcg aatttaagtt aattaccggt     120
ccttctggtt gtggcaaaag tacgctgcta aaaatagttg cttcattgat cagcccaacc     180
agcggaacgt tactgtttga aggtgaggat gtcagcacac taaagccaga atctaccgc     240 caacaagtct cttactgcgc ccagacaccg acgctgtttg gcgataccgg tatacgataat    300 ctgatctttc cctggcagat ccgtaaccgg cagcctgacc cagccatttt tctcgatttt    360
ctcgaacgct tcgccttgcc ggacagcatt ttgacgaaga atatcgccga gctatctggt    420
ggtgaaaaac aacgcatctc attgattcgt aacctgcaat ttatgccgaa ggttttattg    480
ctggatgaaa taccagtgc gctggatgaa agtaataaac ataacgtcaa tgagatgatc    540
catcgttatg tgcgcgagca aaatattgcc gtgctgtggg tgacacacga taaagacgaa    600
attaatcatg cggataaagt gattacactg caaccgcatg ccggagaaat gcaggaagca    660
cgctatgaac tcgcataa                                                   678

<210> SEQ ID NO 4
<211> LENGTH: 225
<212> TYPE: PRT
<213> ORGANISM: Escherichia coli

<400> SEQUENCE: 4
```

Met Gln Glu Asn Ser Pro Leu Leu Gln Leu Gln Asn Val Gly Tyr Leu
1               5                   10                  15

Ala Gly Asp Ala Lys Ile Leu Asn Asn Ile Asn Phe Ser Leu Arg Ala
            20                  25                  30

Gly Glu Phe Lys Leu Ile Thr Gly Pro Ser Gly Cys Gly Lys Ser Thr
        35                  40                  45

Leu Leu Lys Ile Val Ala Ser Leu Ile Ser Pro Thr Ser Gly Thr Leu
    50                  55                  60

Leu Phe Glu Gly Glu Asp Val Ser Thr Leu Lys Pro Glu Ile Tyr Arg
65                  70                  75                  80

Gln Gln Val Ser Tyr Cys Ala Gln Thr Pro Thr Leu Phe Gly Asp Thr
                85                  90                  95

Val Tyr Asp Asn Leu Ile Phe Pro Trp Gln Ile Arg Asn Arg Gln Pro
            100                 105                 110

Asp Pro Ala Ile Phe Leu Asp Phe Leu Glu Arg Phe Ala Leu Pro Asp
        115                 120                 125

Ser Ile Leu Thr Lys Asn Ile Ala Glu Leu Ser Gly Gly Glu Lys Gln
    130                 135                 140

Arg Ile Ser Leu Ile Arg Asn Leu Gln Phe Met Pro Lys Val Leu Leu
145                 150                 155                 160

Leu Asp Glu Ile Thr Ser Ala Leu Asp Glu Ser Asn Lys His Asn Val
                165                 170                 175

Asn Glu Met Ile His Arg Tyr Val Arg Glu Gln Asn Ile Ala Val Leu
            180                 185                 190

Trp Val Thr His Asp Lys Asp Glu Ile Asn His Ala Asp Lys Val Ile
        195                 200                 205

Thr Leu Gln Pro His Ala Gly Glu Met Gln Glu Ala Arg Tyr Glu Leu

Ala
225

<210> SEQ ID NO 5
<211> LENGTH: 903
<212> TYPE: DNA
<213> ORGANISM: Escherichia coli

<400> SEQUENCE: 5

```
atgaatcaat cttatggacg gctggtcagt cgggcggcga ttgctgcgac ggcgatggct      60
tcgctgctat tgctgattaa aattttgca tggtggtata ccgggtcggt gagtattctc     120
gccgcgctgg tggattcgct ggtggatatc ggcgcgtcgt tgacgaattt attggtggtg     180
cgatattccc tgcaacctgc cgacgataat cactcgtttg gtcacggtaa agctgagtcc     240
ctcgcggcgc tggcgcaaag tatgtttatc tccggttcgg cactattcct gttttttgacg     300
ggtattcaac atctgatatc tccaacaccg atgacagatc caggcgtcgg ggttatcgtg     360
acaattgtgg cgctaatttg tacgattatc cttgtctcgt ttcagcgttg ggtggtgcgg     420
cggacgcaaa gccaggcggt gcgggctgat atgctacatt accagtctga tgttatgatg     480
aacggcgcaa ttctgctggc gctggggttg tcctggtacg gctggcatcg cgccgatgct     540
ctgtttgcat gggaatcgg catctatatt ttatatagcg cgttacgcat gggatatgag     600
gcggtacagt cattactgga tcgcgcattg cctgatgagg aacggcaaga aattattgat     660
atcgtgactt cctggccggg tgttagcggc gctcacgatc ttcgcacgcg gcagtcaggg     720
ccgacccgct ttattcagat tcatttggaa atggaagact ctctgccttt ggttcaggca     780
catatggtgg cggatcaggt agagcaggct attttacggc gttttccggg atcggatgta     840
attatccatc aggacccctg ttccgtcgta cccagggagg gtaaacggtc tatgctttca     900
taa                                                                  903
```

<210> SEQ ID NO 6
<211> LENGTH: 300
<212> TYPE: PRT
<213> ORGANISM: Escherichia coli

<400> SEQUENCE: 6

```
Met Asn Gln Ser Tyr Gly Arg Leu Val Ser Arg Ala Ala Ile Ala Ala
 1               5                  10                  15

Thr Ala Met Ala Ser Leu Leu Leu Ile Lys Ile Phe Ala Trp Trp
            20                  25                  30

Tyr Thr Gly Ser Val Ser Ile Leu Ala Ala Leu Val Asp Ser Leu Val
        35                  40                  45

Asp Ile Gly Ala Ser Leu Thr Asn Leu Leu Val Val Arg Tyr Ser Leu
    50                  55                  60

Gln Pro Ala Asp Asp Asn His Ser Phe Gly His Gly Lys Ala Glu Ser
65                  70                  75                  80

Leu Ala Ala Leu Ala Gln Ser Met Phe Ile Ser Gly Ser Ala Leu Phe
                85                  90                  95

Leu Phe Leu Thr Gly Ile Gln His Leu Ile Ser Pro Thr Pro Met Thr
            100                 105                 110

Asp Pro Gly Val Gly Val Ile Val Thr Ile Val Ala Leu Ile Cys Thr
        115                 120                 125

Ile Ile Leu Val Ser Phe Gln Arg Trp Val Val Arg Arg Thr Gln Ser
    130                 135                 140
```

-continued

```
Gln Ala Val Arg Ala Asp Met Leu His Tyr Gln Ser Asp Val Met Met
145                 150                 155                 160

Asn Gly Ala Ile Leu Leu Ala Leu Gly Leu Ser Trp Tyr Gly Trp His
            165                 170                 175

Arg Ala Asp Ala Leu Phe Ala Leu Gly Ile Gly Ile Tyr Ile Leu Tyr
        180                 185                 190

Ser Ala Leu Arg Met Gly Tyr Glu Ala Val Gln Ser Leu Leu Asp Arg
    195                 200                 205

Ala Leu Pro Asp Glu Glu Arg Gln Glu Ile Ile Asp Ile Val Thr Ser
210                 215                 220

Trp Pro Gly Val Ser Gly Ala His Asp Leu Arg Thr Arg Gln Ser Gly
225                 230                 235                 240

Pro Thr Arg Phe Ile Gln Ile His Leu Glu Met Glu Asp Ser Leu Pro
                245                 250                 255

Leu Val Gln Ala His Met Val Ala Asp Gln Val Glu Gln Ala Ile Leu
            260                 265                 270

Arg Arg Phe Pro Gly Ser Asp Val Ile Ile His Gln Asp Pro Cys Ser
        275                 280                 285

Val Val Pro Arg Glu Gly Lys Arg Ser Met Leu Ser
    290                 295                 300

<210> SEQ ID NO 7
<211> LENGTH: 64
<212> TYPE: DNA
<213> ORGANISM: Artificial Sequence
<220> FEATURE:
<223> OTHER INFORMATION: Primer P1

<400> SEQUENCE: 7
tgctgtgggg gttttttta tcctcaattt gcctgctgaa gcctgctttt ttatactaag    60
ttgg                                                                64

<210> SEQ ID NO 8
<211> LENGTH: 75
<212> TYPE: DNA
<213> ORGANISM: Artificial Sequence
<220> FEATURE:
<223> OTHER INFORMATION: Primer P2

<400> SEQUENCE: 8
cgccgcccga ctgaccagcc gtccataaga ttgattcatt atatctcctt cttaaagtta    60
aacaaaatta ttagg                                                    75

<210> SEQ ID NO 9
<211> LENGTH: 64
<212> TYPE: DNA
<213> ORGANISM: Artificial Sequence
<220> FEATURE:
<223> OTHER INFORMATION: Primer P3

<400> SEQUENCE: 9
ctcctgttgt accgtccata atcagcaaaa ttgctgtgaa gcctgctttt ttatactaag    60
ttgg                                                                64

<210> SEQ ID NO 10
<211> LENGTH: 75
<212> TYPE: DNA
<213> ORGANISM: Artificial Sequence
<220> FEATURE:
```

<223> OTHER INFORMATION: Primer P4

<400> SEQUENCE: 10

```
cagtgctaat gattcgttag taatattatg cgagttcatt atatctcctt cttaaagtta    60
aacaaaatta ttagg                                                    75
```

<210> SEQ ID NO 11
<211> LENGTH: 88
<212> TYPE: DNA
<213> ORGANISM: Artificial Sequence
<220> FEATURE:
<223> OTHER INFORMATION: Promoter Pnlp8phi10

<400> SEQUENCE: 11

```
ttgacaaggg tccttgcacg gttataatgt cactggttat taaccaattt ttcctaataa    60
ttttgtttaa ctttaagaag gagatata                                       88
```

<210> SEQ ID NO 12
<211> LENGTH: 1951
<212> TYPE: DNA
<213> ORGANISM: Artificial Sequence
<220> FEATURE:
<223> OTHER INFORMATION: DNA-fragment 1

<400> SEQUENCE: 12

```
tgctgtgggg gttttttta tcctcaattt gcctgctgaa gcctgctttt ttatactaag     60
ttggcattat aaaaaagcat tgcttatcaa tttgttgcaa cgaacaggtc actatcagtc   120
aaaataaaat cattatttga tttcgaattc cccggatccg tcgacctgca gggggggggg   180
ggcgctgagg tctgcctcgt gaagaaggtg ttgctgactc ataccaggcc tgaatcgccc   240
catcatccag ccagaaagtg agggagccac ggttgatgag agctttgttg taggtggacc   300
agttggtgat tttgaacttt tgctttgcca cggaacggtc tgcgttgtcg gaagatgcg    360 tgatctgatc cttcaactca gcaaaagttc gatttattca acaaagccgc cgtcccgtca   420
agtcagcgta atgctctgcc agtgttacaa ccaattaacc aattctgatt agaaaaactc   480
atcgagcatc aaatgaaact gcaatttatt catatcagga ttatcaatac catattttg    540 aaaaagccgt ttctgtaatg aaggagaaaa ctcaccgagg cagttccata ggatggcaag   600
atcctggtat cggtctgcga ttccgactcg tccaacatca atacaaccta ttaatttccc   660
ctcgtcaaaa ataaggttat caagtgagaa atcaccatga gtgacgactg aatccggtga   720
gaatggcaaa agcttatgca tttctttcca gacttgttca acaggccagc cattacgctc   780
gtcatcaaaa tcactcgcat caaccaaacc gttattcatt cgtgattgcg cctgagcgag   840
acgaaatacg cgatcgctgt taaaaggaca attacaaaca ggaatcgaat gcaaccggcg   900
caggaacact gccagcgcat caacaatatt ttcacctgaa tcaggatatt cttctaatac   960
ctggaatgct gttttcccgg ggatcgcagt ggtgagtaac catgcatcat caggagtacg  1020
gataaaatgc ttgatggtcg gaagaggcat aaattccgtc agccagttta gtctgaccat  1080
ctcatctgta acatcattgg caacgctacc tttgccatgt ttcagaaaca actctggcgc  1140
atcgggcttc ccatacaatc gatagattgt cgcacctgat tgcccgacat atcgcgagc   1200 ccatttatac ccatataaat cagcatccat gttggaattt aatcgcggcc tcgagcaaga  1260
cgtttcccgt tgaatatggc tcataacacc ccttgtatta ctgtttatgt aagcagacag  1320
ttttattgtt catgatgata tatttttatc ttgtgcaatg taacatcaga gattttgaga  1380
cacaacgtgg ctttccccccc cccccctgca gtctgttaca ggtcactaat accatctaag  1440
```

```
tagttgattc atagtgactg catatgttgt gttttacagt attatgtagt ctgtttttta      1500
tacaaaatct aatttaatat attgatattt atatcatttt acgtttctcg ttcagctttt      1560
ttatactaac ttgagcgtct agcttccaac tgcgctaatg acgcagctgg acgaaggcgg      1620
gattctcgtc ttacccgtag gggaggagca ccagtatttg aaacgggtgt gtcgtcgggg      1680
aggcgaattt attatcgata ccgtggaggc cgtgcgcttt gtcccttag tgaagggtga       1740 gctggcttaa aacgtgagga aatacctgga ttttcctgg ttattttgcc gcaggtcagc       1800
gtataatgaa gatcttttcc agtgttgaca agggtccttg cacggttata atgtcactgg      1860
ttattaacca attttccta ataattttgt ttaactttaa gaaggagata taatgaatca       1920
atcttatgga cggctggtca gtcgggcggc g                                     1951

<210> SEQ ID NO 13
<211> LENGTH: 1951
<212> TYPE: DNA
<213> ORGANISM: Artificial Sequence
<220> FEATURE:
<223> OTHER INFORMATION: DNA-fragment 2

<400> SEQUENCE: 13
ctcctgttgt accgtccata atcagcaaaa ttgctgtgaa gcctgctttt ttatactaag        60
ttggcattat aaaaaagcat tgcttatcaa tttgttgcaa cgaacaggtc actatcagtc       120
aaaataaaat cattatttga tttcgaattc cccggatccg tcgacctgca ggggggggg       180 ggcgctgagg tctgcctcgt gaagaaggtg ttgctgactc ataccaggcc tgaatcgccc       240
catcatccag ccagaaagtg agggagccac ggttgatgag agctttgttg taggtggacc       300
agttggtgat tttgaacttt tgctttgcca cggaacggtc tgcgttgtcg ggaagatgcg       360
tgatctgatc cttcaactca gcaaaagttc gatttattca acaaagccgc cgtcccgtca       420
agtcagcgta atgctctgcc agtgttacaa ccaattaacc aattctgatt agaaaaactc       480
atcgagcatc aaatgaaact gcaatttatt catatcagga ttatcaatac catatttttg       540
aaaaagccgt ttctgtaatg aaggagaaaa ctcaccgagg cagttccata ggatggcaag       600
atcctggtat cggtctgcga ttccgactcg tccaacatca atacaaccta ttaatttccc       660
ctcgtcaaaa ataaggttat caagtgagaa atcaccatga gtgacgactg aatccggtga       720
gaatggcaaa agcttatgca tttctttcca gacttgttca acaggccagc cattacgctc       780
gtcatcaaaa tcactcgcat caaccaaacc gttattcatt cgtgattgcg cctgagcgag       840
acgaaatacg cgatcgctgt taaaaggaca attacaaaca ggaatcgaat gcaaccggcg       900
caggaacact gccagcgcat caacaatatt ttcacctgaa tcaggatatt cttctaatac       960
ctggaatgct gttttcccgg ggatcgcagt ggtgagtaac catgcatcat caggagtacg      1020
gataaaatgc ttgatggtcg gaagaggcat aaattccgtc agccagttta gtctgaccat      1080
ctcatctgta acatcattgg caacgctacc tttgccatgt ttcagaaaca actctggcgc      1140
atcgggcttc ccatacaatc gatagattgt cgcacctgat tgcccgacat tatcgcgagc      1200
ccatttatac ccatataaat cagcatccat gttggaattt aatcgcggcc tcgagcaaga      1260
cgtttcccgt tgaatatggc tcataacacc ccttgtatta ctgtttatgt aagcagacag      1320
ttttattgtt catgatgata tatttttatc ttgtgcaatg taacatcaga gattttgaga      1380
cacaacgtgg ctttcccccc cccccctgca gtctgttaca ggtcactaat accatctaag      1440
tagttgattc atagtgactg catatgttgt gttttacagt attatgtagt ctgtttttta      1500
```

```
tacaaaatct aatttaatat attgatattt atatcatttt acgtttctcg ttcagctttt   1560
ttatactaac ttgagcgtct agcttccaac tgcgctaatg acgcagctgg acgaaggcgg   1620
gattctcgtc ttacccgtag gggaggagca ccagtatttg aaacgggtgt gtcgtcgggg   1680
aggcgaattt attatcgata ccgtggaggc cgtgcgcttt gtcccttag  tgaagggtga   1740 gctggcttaa aacgtgagga aatacctgga tttttcctgg ttattttgcc gcaggtcagc   1800
gtataatgaa gatcttttcc agtgttgaca agggtcctg  cacggttata atgtcactgg   1860
ttattaacca attttccta  ataattttgt ttaactttaa gaaggagata taatgaactc   1920
gcataatatt actaacgaat cattagcact g                                  1951
```

<210> SEQ ID NO 14
<211> LENGTH: 20
<212> TYPE: DNA
<213> ORGANISM: Artificial Sequence
<220> FEATURE:
<223> OTHER INFORMATION: Primer P5

<400> SEQUENCE: 14

```
gcaaaaaagt tcatcgttga                                                 20
```

<210> SEQ ID NO 15
<211> LENGTH: 20
<212> TYPE: DNA
<213> ORGANISM: Artificial Sequence
<220> FEATURE:
<223> OTHER INFORMATION: Primer P6

<400> SEQUENCE: 15

```
ccagcgcggc gagaatactc                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Primer P7

<400> SEQUENCE: 16

```
ctgtccactg atagccctgc                                                 20
```

<210> SEQ ID NO 17
<211> LENGTH: 18
<212> TYPE: DNA
<213> ORGANISM: Artificial Sequence
<220> FEATURE:
<223> OTHER INFORMATION: Primer P8

<400> SEQUENCE: 17

```
gaattatcgc tcgcccga                                                   18
```

<210> SEQ ID NO 18
<211> LENGTH: 333
<212> TYPE: DNA
<213> ORGANISM: Artificial Sequence
<220> FEATURE:
<223> OTHER INFORMATION: DNA-fragment 3

<400> SEQUENCE: 18

```
gcaaaaaagt tcatcgttga agctattgag tagtagcaac tcacgttccc agtagtaaac    60
cctgttttcc ttgccataga caccatccct gtcttccccc acatgctgtg ggggtttttt   120
ttatcctcaa tttgcctgct gcttaatgca ttgcagatga tttgcttccg ttatactagc   180
```

```
gtcagttgat agcgggagta tttatgaatc aatcttatgg acggctggtc agtcgggcgg    240
cgattgctgc gacggcgatg gcttcgctgc tattgctgat taaaattttt gcatggtggt    300
ataccgggtc ggtgagtatt ctcgccgcgc tgg                                 333
```

<210> SEQ ID NO 19
<211> LENGTH: 1036
<212> TYPE: DNA
<213> ORGANISM: Artificial Sequence
<220> FEATURE:
<223> OTHER INFORMATION: DNA-fragment 4

<400> SEQUENCE: 19

```
ctgtccactg atagccctgc ggtacgattt tgacacccgc gccgacaatg accagcgcga     60
caaaaatgag aatcgggata aagataagca tcggaaaaac ctcctgttgt accgtccata    120
atcagcaaaa ttgctgcttg attaaacaaa ttatacctga ttactgaaag agagttcccc    180
cttattcctg cgaaggataa actgttttta gtaaaaatca gaaaaaggga acagcgatgc    240
aggaaaatag tcctttgctt cagctacaaa acgtaggata tctggcgggt gatgcgaaga    300
ttcttaataa catcaatttt tcgctgcgtg ctggcgaatt taagttaatt accggtcctt    360
ctggttgtgg caaaagtacg ctgctaaaaa tagttgcttc attgatcagc ccaaccagcg    420
gaacgttact gtttgaaggt gaggatgtca gcacactaaa gccagaaatc taccgccaac    480
aagtctctta ctgcgcccag acaccgacgc tgtttggcga tacggtatac gataatctga    540
tctttccctg gcagatccgt aaccggcagc ctgacccagc cattttttctc gattttctcg    600 aacgcttcgc cttgccggac agcattttga cgaagaatat cgccgagcta tctggtggtg    660
aaaaacaacg catctcattg attcgtaacc tgcaatttat gccgaaggtt ttattgctgg    720
atgaaataac cagtgcgctg gatgaaagta ataaacataa cgtcaatgag atgatccatc    780
gttatgtgcg cgagcaaaat attgccgtgc tgtgggtgac acacgataaa gacgaaatta    840
atcatgcgga taaagtgatt acactgcaac cgcatgccgg agaaatgcag gaagcacgct    900
atgaactcgc ataatattac taacgaatca ttagcactgg cattaatgct ggtggtggtg    960
gcaatcttaa ttagccataa agaaaaactg gcgctggaga agatattct ctggagcgtc   1020 gggcgagcga taattc                                                  1036
```

<210> SEQ ID NO 20
<211> LENGTH: 2145
<212> TYPE: DNA
<213> ORGANISM: Artificial Sequence
<220> FEATURE:
<223> OTHER INFORMATION: DNA-fragment 5

<400> SEQUENCE: 20

```
gcaaaaaagt tcatcgttga agctattgag tagtagcaac tcacgttccc agtagtaaac     60
cctgttttcc ttgccataga caccatccct gtcttccccc acatgctgtg ggggttttt    120 ttatcctcaa tttgcctgct gaagcctgct tttttatact aagttggcat tataaaaaag    180
cattgcttat caatttgttg caacgaacag gtcactatca gtcaaaataa aatcattatt    240
tgatttcgaa ttccccggat ccgtcgacct gcagggggggg ggggcgctg aggtctgcct    300 cgtgaagaag gtgttgctga ctcataccag gcctgaatcg ccccatcatc cagccagaaa    360
gtgagggagc cacggttgat gagagctttt ttgtaggtgg accagttggt gattttgaac    420
ttttgctttg ccacggaacg gtctgcgttg tcgggaagat gcgtgatctg atccttcaac    480
```

```
tcagcaaaag ttcgatttat tcaacaaagc cgccgtcccg tcaagtcagc gtaatgctct        540
gccagtgtta caaccaatta accaattctg attagaaaaa ctcatcgagc atcaaatgaa        600
actgcaattt attcatatca ggattatcaa taccatattt ttgaaaaagc cgtttctgta        660
atgaaggaga aaactcaccg aggcagttcc ataggatggc aagatcctgg tatcggtctg        720
cgattccgac tcgtccaaca tcaatacaac ctattaattt ccctcgtca aaataaggt         780 tatcaagtga gaatcacca tgagtgacga ctgaatccgg tgagaatggc aaaagcttat        840
gcatttcttt ccagacttgt tcaacaggcc agccattacg ctcgtcatca aaatcactcg        900
catcaaccaa accgttattc attcgtgatt gcgcctgagc gagacgaaat acgcgatcgc        960
tgttaaaagg acaattacaa acaggaatcg aatgcaaccg gcgcaggaac actgccagcg       1020
catcaacaat attttcacct gaatcaggat attcttctaa tacctggaat gctgttttcc       1080
cggggatcgc agtggtgagt aaccatgcat catcaggagt acggataaaa tgcttgatgg       1140
tcggaagagg cataaattcc gtcagccagt ttagtctgac catctcatct gtaacatcat       1200
tggcaacgct acctttgcca tgtttcagaa acaactctgg cgcatcgggc ttcccataca       1260
atcgatagat tgtcgcacct gattgcccga cattatcgcg agcccattta tacccatata       1320
aatcagcatc catgttggaa tttaatcgcg gcctcgagca agacgtttcc cgttgaatat       1380
ggctcataac accccttgta ttactgttta tgtaagcaga cagttttatt gttcatgatg       1440
atataatttt atcttgtgca atgtaacatc agagattttg agacacaacg tggctttccc       1500
ccccccccct gcagtctgtt acaggtcact aataccatct aagtagttga ttcatagtga       1560
ctgcatatgt tgtgttttac agtattatgt agtctgtttt ttatacaaaa tctaatttaa       1620
tatattgata tttatatcat tttacgtttc tcgttcagct ttttatact aacttgagcg       1680 tctagcttcc aactgcgcta atgacgcagc tggacgaagg cgggattctc gtcttacccg       1740
taggggagga gcaccagtat ttgaaacggg tgtgtcgtcg gggaggcgaa tttattatcg       1800
ataccgtgga ggccgtgcgc tttgtcccctt tagtgaaggg tgagctggct taaaacgtga       1860
ggaaatacct ggatttttcc tggttatttt gccgcaggtc agcgtataat gaagatcttt       1920
tccagtgttg acaagggtcc ttgcacggtt ataatgtcac tggttattaa ccaatttttc       1980
ctaataattt tgtttaactt taagaaggag atataatgaa tcaatcttat ggacggctgg       2040
tcagtcgggc ggcgattgct gcgacggcga tggcttcgct gctattgctg attaaaattt       2100
ttgcatggtg gtataccggg tcggtgagta ttctcgccgc gctgg                      2145

<210> SEQ ID NO 21
<211> LENGTH: 2148
<212> TYPE: DNA
<213> ORGANISM: Artificial Sequence
<220> FEATURE:
<223> OTHER INFORMATION: DNA-fragment 6

<400> SEQUENCE: 21
ctgtccactg atagccctgc ggtacgattt tgacacccgc gccgacaatg accagcgcga        60
caaaaatgag aatcgggata agataagca tcggaaaaac ctcctgttgt accgtccata       120
atcagcaaaa ttgctgtgaa gcctgctttt ttatactaag ttggcattat aaaaaagcat       180
tgcttatcaa tttgttgcaa cgaacaggtc actatcagtc aaaataaaat cattatttga       240
tttcgaattc cccggatccg tcgacctgca ggggggggg ggcgctgagg tctgcctcgt       300
gaagaaggtg ttgctgactc ataccaggcc tgaatcgccc catcatccag ccagaaagtg       360
agggagccac ggttgatgag agctttgttg taggtggacc agttggtgat tttgaacttt       420
```

```
tgctttgcca cggaacggtc tgcgttgtcg ggaagatgcg tgatctgatc cttcaactca    480
gcaaaagttc gatttattca acaaagccgc cgtcccgtca agtcagcgta atgctctgcc    540
agtgttacaa ccaattaacc aattctgatt agaaaaactc atcgagcatc aaatgaaact    600
gcaatttatt catatcagga ttatcaatac catattttg aaaaagccgt ttctgtaatg     660
aaggagaaaa ctcaccgagg cagttccata ggatggcaag atcctggtat cggtctgcga    720
ttccgactcg tccaacatca atacaaccta ttaatttccc ctcgtcaaaa ataaggttat    780
caagtgagaa atcaccatga gtgacgactg aatccggtga gaatggcaaa agcttatgca    840
tttctttcca gacttgttca acaggccagc cattacgctc gtcatcaaaa tcactcgcat    900
caaccaaacc gttattcatt cgtgattgcg cctgagcgag acgaaatacg cgatcgctgt    960
taaaaggaca attacaaaca ggaatcgaat gcaaccggcg caggaacact gccagcgcat    1020
caacaatatt ttcacctgaa tcaggatatt cttctaatac ctggaatgct gttttcccgg    1080
ggatcgcagt ggtgagtaac catgcatcat caggagtacg gataaaatgc ttgatggtcg    1140
gaagaggcat aaattccgtc agccagttta gtctgaccat ctcatctgta acatcattgg    1200
caacgctacc tttgccatgt ttcagaaaca actctggcgc atcgggcttc ccatacaatc    1260
gatagattgt cgcacctgat tgcccgacat tatcgcgagc ccatttatac ccatataaat    1320
cagcatccat gttggaattt aatcgcggcc tcgagcaaga cgtttcccgt tgaatatggc    1380
tcataacacc ccttgtatta ctgtttatgt aagcagacag ttttattgtt catgatgata    1440
tatttttatc ttgtgcaatg taacatcaga gattttgaga cacaacgtgg ctttccccccc    1500 cccccctgca gtctgttaca ggtcactaat accatctaag tagttgattc atagtgactg    1560
catatgttgt gttttacagt attatgtagt ctgtttttta tacaaaatct aatttaatat    1620
attgatattt atatcatttt acgtttctcg ttcagctttt ttatactaac ttgagcgtct    1680
agcttccaac tgcgctaatg acgcagctgg acgaaggcgg gattctcgtc ttacccgtag    1740
gggaggagca ccagtatttg aaacgggtgt gtcgtcgggg aggcgaattt attatcgata    1800
ccgtggaggc cgtgcgcttt gtcccttag tgaagggtga gctggcttaa acgtgagga     1860 aatacctgga tttttcctgg ttattttgcc gcaggtcagc gtataatgaa gatcttttcc    1920
agtgttgaca agggtccttg cacggttata atgtcactgg ttattaacca attttttccta   1980 ataattttgt ttaactttaa gaaggagata taatgaactc gcataatatt actaacgaat    2040
cattagcact ggcattaatg ctggtggtgg tggcaatctt aattagccat aaagaaaaac    2100
tggcgctgga gaaagatatt ctctggagcg tcgggcgagc gataattc                 2148
```

METHOD FOR PRODUCING L-AMINO ACIDS USING A BACTERIUM OF THE FAMILY ENTEROBACTERIACEAE OVEREXPRESSING A GENE ENCODING AN IRON EXPORTER

This application is a Continuation of, and claims priority under 35 U.S.C. § 120 to, International Application No. PCT/JP2017/007035, filed Feb. 24, 2017, and claims priority therethrough under 35 U.S.C. § 119 to Russian Patent Application No. 2016106614, filed Feb. 25, 2016, the entireties of which are incorporated by reference herein. Also, the Sequence Listing filed electronically herewith is hereby incorporated by reference (File name: 2018-08-21T_US-559_Seq List; File size: 25 KB; Date recorded: Aug. 21, 2018).

BACKGROUND OF THE INVENTION

Field of the Invention

The present invention relates generally to the microbiological industry, and specifically to a method for producing L-amino acids by fermentation of a bacterium of the family Enterobacteriaceae that has been modified to overexpress a gene encoding an iron exporter, so that production of L-amino acids is enhanced.

Brief Description of the Related Art

Conventionally, L-amino acids are industrially produced by fermentation methods utilizing strains of microorganisms obtained from natural sources, or mutants thereof. Typically, the microorganisms are modified to improve production of L-amino acids, so that the yield of L-amino acids is enhanced.

Many techniques to enhance L-amino acid production yields have been reported, including transformation of microorganisms with recombinant DNA (see, for example, U.S. Pat. No. 4,278,765 A) and alteration of expression regulatory regions such as promoters, leader sequences, and/or attenuators, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes that is/are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

Iron is an essential metal for most organisms. Iron ions are required for the function of cells such as respiration and DNA synthesis, but these can be toxic to the cells due to formation of reactive oxygen species (ROS; Andrews S. C. et al., Bacterial iron homeostasis, FEMS Microbiol. Rev., 2003, 27(2-3):215-237). Therefore, organisms must balance their needs to provide efficient uptake of iron ions from the environment and scavenge or export excessive cellular free iron ions to guard against iron-induced toxicity. Bacteria secrete high-affinity extracellular ferric chelators, called siderophores (iron carriers), to solubilize iron ions prior to transport into cells (Koester W., ABC transporter-mediated uptake of iron, siderophores, heme and vitamin B12, Res. Microbiol., 2001, 152(3-4):291-301). Gram-negative bacteria take up ferri-siderophore complexes using specific outer membrane (OM) receptors in a process that is driven by the cytoplasmic membrane (CM) potential and mediated by the energy-transducing TonB-ExbB-ExbD system (Andrews S. C. et al., 2003). The OM siderophore receptors are related (Koester W., 2001), and the crystal structures of some of them (FepA, FecA and FhuA) were determined (Buchanan S. K. et al., Crystal structure of the outer membrane active transporter FepA from Escherichia coli, Nat. Struct. Biol., 1999, 6:56-63; Ferguson A. D. et al., Siderophore-mediated iron transport: crystal structure of FhuA with bound lipopolysaccharide, Science, 1998, 282:2215-2220; Ferguson A. D. et al., Structural basis of gating by the outer membrane transporter FecA, Science, 2002, 295:1715-1719). An Escherichia bacterium that overexpresses the fepA gene, which encodes an OM protein that binds and transports ferric enterobactin, the fecA gene, which encodes a ferric citrate uptake receptor, or the tonB gene, which encodes a CM protein that transduces the proton motive force of the CM to the OM active transporters, was utilized in a method for producing L-amino acids, such as L-threonine and L-lysine, by fermentation of the bacterium (EP1979486 B1).

Little is known about the export of iron ions in prokaryotes (Sankari S. and O'Brian M. R., A bacterial iron exporter for maintenance of iron homeostasis, J. Biol. Chem., 2014, 289(23):16498-16507). Two iron exporters of Escherichia, such as FetAB and FieF, have been described (Sankari S. et al., 2014; Nicolaou S. A. et al., Overexpression of fetA (ybbL) and fetB (ybbM), encoding an iron exporter, enhances resistance to oxidative stress in Escherichia coli, Appl. Environ. Microbiol., 2013, 79(23):7210-7219). The FetAB complex is predicted to be an ATP-binding cassette (ABC)-type transporter involved in iron homeostasis in Escherichia coli, with FetA being the ATP-binding component subunit and FetB being the inner membrane metal resistance protein encoded by the fetA and fetB genes, respectively. The FieF protein, encoded by the fieF gene, is a member of the cation diffusion facilitator (CDF) family of metal cation transporters that functions as a divalent metal cations exporter, in particular, iron ions (Grass G. et al., FieF (YiiP) from Escherichia coli mediates decreased cellular accumulation of iron and relieves iron stress, Arch. Microbiol., 2005, 183:9-18).

However, no data has been previously reported that describes the effect of overexpression of a gene encoding an iron exporter on production of L-amino acids by fermentation of an L-amino acid-producing bacterium of the family Enterobacteriaceae.

SUMMARY OF THE INVENTION

An improved method of producing L-amino acids by fermentation of a bacterium of the family Enterobacteriaceae is described herein. According to the presently disclosed subject matter, production of L-amino acids by fermentation of a bacterium of the family Enterobacteriaceae can be increased. Specifically, production of L-amino acids by fermentation of a bacterium of the family Enterobacteriaceae can be improved by overexpressing a gene encoding an iron exporter in the bacterium, so that the production of L-amino acids by the modified bacterium is increased.

This aim was achieved by the finding that overexpression of a gene encoding an iron exporter in a bacterium of the family Enterobacteriaceae, which can belong to the genus *Escherichia* and, more specifically, to the species *Escherichia coli*, having an L-amino acid producing ability confers on the bacterium a higher productivity of L-amino acid when the bacterium is cultured in the medium. Specifically, the aim was achieved by the finding that overexpression of fetB gene or fieF gene encoding an iron exporter in a bacterium of the family Enterobacteriaceae, which can belong to the genus *Escherichia* and, more specifically, to the species *Escherichia coli*, having an L-amino acid producing ability confers on the bacterium a higher productivity of L-amino acid when the bacterium is cultured in the medium.

It is one aspect of the present invention to provide a method for producing an L-amino acid comprising: (i) cultivating an L-amino acid-producing bacterium of the family Enterobacteriaceae in a culture medium to produce and accumulate the L-amino acid in the culture medium or cells of the bacterium, or both, and (ii) collecting the L-amino acid from the culture medium or cells of the bacterium, or both, wherein the bacterium has been modified to overexpress a gene encoding an iron exporter.

It is a further aspect of the present invention to provide the method as described above, wherein the gene encoding an iron exporter is overexpressed by increasing the copy number of the gene, and/or modifying an expression regulatory region of the gene, so that the expression of the gene is enhanced as compared with a non-modified bacterium.

It is a further aspect of the present invention to provide the method as described above, wherein the gene encoding an iron exporter is selected from the group consisting of fetB gene, fetA gene, fieF gene, and combinations thereof.

It is a further aspect of the present invention to provide the method as described above, wherein the gene encoding an iron exporter encodes a protein selected from the group consisting of: (A) a protein comprising the amino acid sequence of SEQ ID NO: 2, 4 or 6; (B) a protein comprising the amino acid sequence of SEQ ID NO: 2, 4 or 6, but which includes substitution, deletion, insertion, and/or addition of one or several amino acid residues, wherein the protein has an iron exporter activity; and (C) a protein comprising an amino acid sequence that is not less than 90% homologous with respect to the entire amino acid sequence of SEQ ID NO: 2, 4 or 6, wherein the protein has an iron exporter activity.

It is a further aspect of the present invention to provide the method as described above, wherein the gene encoding an iron exporter is a DNA selected from the group consisting of: (A) a DNA comprising the nucleotide sequence of SEQ ID NO: 1, 3 or 5; (B) a DNA encoding a protein comprising the amino acid sequence of SEQ ID NO: 2, 4 or 6, but which includes substitution, deletion, insertion and/or addition of one or several amino acid residues, wherein the protein has an iron exporter activity; and (C) a DNA comprising a variant nucleotide sequence of SEQ ID NO: 1, 3, or 5 due to the degeneracy of the genetic code.

It is a further aspect of the present invention to provide the method as described above, wherein the bacterium belongs to the genus *Escherichia*.

It is a further aspect of the present invention to provide the method as described above, wherein the bacterium is *Escherichia coli*.

It is a further aspect of the present invention to provide the method as described above, wherein the bacterium belongs to the genus *Pantoea*.

It is a further aspect of the present invention to provide the method as described above, wherein the bacterium is *Pantoea ananatis*.

It is a further aspect of the present invention to provide the method as described above, wherein the L-amino acid an L-amino acid belonging to the aspartate family.

It is a further aspect of the present invention to provide the method as described above, wherein the L-amino acid belonging to the aspartate family is selected from the group consisting of L-asparagine, L-aspartic acid, L-isoleucine, L-lysine, L-methionine, and L-threonine.

DESCRIPTION OF THE PREFERRED EMBODIMENTS

1. Bacterium

Any L-amino acid-producing bacterium belonging to the family Enterobacteriaceae and modified to overexpress a gene encoding an iron exporter can be used. The phrase "an L-amino acid-producing bacterium" can mean a bacterium of the family Enterobacteriaceae which has an ability to produce, excrete or secrete, and/or cause accumulation of L-amino acid in a culture medium and/or the bacterial cells when the bacterium is cultured in the medium.

The phrase "an L-amino acid-producing bacterium" can also mean a bacterium which has an ability to produce, excrete or secrete, and/or cause accumulation of L-amino acid in a culture medium in an amount larger than a wild-type or parental strain, such as *Escherichia coli* K-12. The phrase "an L-amino acid-producing bacterium" can also mean a bacterium that is able to cause accumulation in the medium of an amount, for example, not less than 0.5 g/L or not less than 1.0 g/L of the target L-amino acid.

Furthermore, the bacterium belonging to the family Enterobacteriaceae and modified to overexpress a gene encoding an iron exporter, which has an ability to produce an L-amino acid, can also be used. The bacterium may inherently have the ability to produce an L-amino acid or may be modified to have an ability to produce an L-amino acid by using a mutation method or DNA recombination techniques. The bacterium can be obtained by overexpressing a gene encoding an iron exporter in a bacterium that inherently has the ability to produce an L-amino acid, or in a bacterium that has been already imparted with the ability to produce an L-amino acid. Alternatively, the bacterium can be obtained by imparting the ability to produce an L-amino acid to a bacterium already modified to overexpress a gene encoding an iron exporter.

The phrase "an ability to produce an L-amino acid" can mean the ability of a bacterium of the family Enterobacteriaceae to produce, excrete or secrete, and/or cause accumulation of an L-amino acid in a culture medium and/or the bacterial cells to such a level that the L-amino acid can be collected from the culture medium and/or the bacterial cells when the bacterium is cultured in the medium.

The bacterium can produce an L-amino acid (i.e. a target L-amino acid) either alone or as a mixture of the L-amino acid (i.e. the target L-amino acid) and one or more kinds of other L-amino acids that are different from the target L-amino acid. That is, the bacterium can produce one kind of L-amino acid alone, or a mixture of two or more kinds of L-amino acids.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "aromatic L-amino acid" includes, for example, L-phenylalanine, L-tryptophan, and L-tyrosine. As L-histidine has an aromatic moiety such as imidazole ring, the phrase "aromatic L-amino acid" can also include, besides the aforementioned aromatic L-amino acids, the L-histidine.

The phrase "non-aromatic L-amino acid" includes, for example, L-alanine, L-arginine, L-asparagine, L-aspartic acid, L-citrulline, L-cysteine, L-glutamic acid, L-glutamine, glycine, L-isoleucine, L-leucine, L-lysine, L-methionine, L-ornithine, L-proline, L-serine, L-threonine, and L-valine. As the biosynthetic pathway of aromatic amino acids such as L-phenylalanine, L-tryptophan, and L-tyrosine is different from the biosynthetic pathway of L-histidine, the phrase "non-aromatic L-amino acid" can also include, besides the aforementioned non-aromatic L-amino acids, the L-histidine.

An L-amino acid can belong to one or more L-amino acid families. As an example, the L-amino acid can belong to the glutamate family including L-arginine, L-glutamic acid, L-glutamine, and L-proline; the serine family including L-cysteine, glycine, and L-serine; the aspartate family including L-asparagine, L-aspartic acid, L-isoleucine, L-lysine, L-methionine, and L-threonine; the pyruvate family including L-alanine, L-isoleucine, L-valine, and L-leucine; and the aromatic family including L-phenylalanine, L-tryptophan, and L-tyrosine. As some L-amino acids can be the intermediate amino acids in a biosynthetic pathway of a particular L-amino acid, the aforementioned families of amino acids may also include other L-amino acids, for example, non-proteinogenic L-amino acids. For example, L-citrulline and L-ornithine are amino acids from the L-arginine biosynthetic pathway. Therefore, the glutamate family may include L-citrulline and L-ornithine, as well as L-arginine, L-glutamic acid, L-glutamine, and L-proline.

L-Arginine, L-cysteine, L-glutamic acid, L-histidine, L-isoleucine, L-lysine, L-ornithine, L-phenylalanine, L-proline, L-threonine, L-tryptophan, and L-valine are particular examples of the L-amino acid. The aspartate family amino acids such as L-asparagine, L-aspartic acid, L-isoleucine, L-lysine, L-methionine, and L-threonine are preferable examples of the L-amino acid. L-Threonine is more preferable example of the L-amino acid.

The phrase "L-amino acid" includes not only an L-amino acid in a free form, but may also include a salt or a hydrate of the L-amino acid, or an adduct formed by the L-amino acid and another organic or inorganic compound.

The bacteria belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, and can have the ability to produce an L-amino acid. Specifically, those classified into the family Enterobacteriaceae according to the taxonomy used in the NCBI (National Center for Biotechnology Information) database (ncbi.nlm.nih.gov/Taxonomy/Browser/wwwtax.cgi?id=543) can be used. Examples of strains from the family Enterobacteriaceae which can be modified include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *Escherichia coli* K-12, p. 2460-2488. In F. C. Neidhardt et al. (ed.), *Escherichia coli* and *Salmonella*: cellular and molecular biology, $2^{nd}$ ed. ASM Press, Washington, D.C., 1996). The species *Escherichia coli* is a particular example. Specific examples of *Escherichia coli* include *Escherichia coli* W3110 (ATCC 27325), *Escherichia coli* MG1655 (ATCC 47076), and so forth, which are derived from the prototype wild-type strain, *Escherichia coli* K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis*, and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

Hereafter, L-amino acid-producing bacteria will be specifically exemplified. Any of the properties of the L-amino acid-producing bacteria and modifications for imparting or enhancing an L-amino acid-producing ability, such as those exemplified below, can be used independently or in any appropriate combination.

L-Arginine-Producing Bacteria

Examples of L-arginine-producing bacteria and parental strains which can be used to derive L-arginine-producing bacteria include, but are not limited to, strains belonging to the genus *Escherichia* such as *Escherichia coli* strain 237 (VKPM B-7925) (U.S. Patent Application No. 2002058315 A1) and its derivative strains harboring mutant N-acetylglutamate synthase (Russian Patent No. 2215783 C2), *Escherichia coli* strain 382 (VKPM B-7926, EP1170358 A1), which is a strain derived from the strain 237 and having an improved acetic acid-assimilating ability, *Escherichia coli* strain 382 ilvA+, which is a strain obtained from the strain 382 by introducing the wild-type allele of ilvA gene from *Escherichia coli* K-12 strain thereto, and the like. Examples of mutant N-acetylglutamate synthase include, for example, a mutant N-acetylglutamate synthase desensitized to feedback inhibition by L-arginine by substitution for the amino acid residues corresponding to the positions 15 to 19 of the wild type enzyme (EP1170361 A1).

Examples of L-arginine-producing bacteria and parental strains which can be used to derive L-arginine-producing bacteria also include strains in which expression of one or more genes encoding an L-arginine biosynthetic enzyme are enhanced. Examples of such genes include genes encoding N-acetyl-γ-glutamylphosphate reductase (argq, ornithine acetyltransferase (argJ), N-acetylglutamate kinase (argB), N-acetylornithine aminotransferase (argD), ornithine carbamoyltransferase (argF), argininosuccinate synthase (argG), argininosuccinate lyase (argH), and carbamoyl phosphate synthetase (carAB), in addition to the gene encoding N-acetylglutamate synthase (argA).

Examples of L-arginine-producing bacteria and parental strains which can be used to derive L-arginine-producing bacteria also include strains having resistance to amino acid analogues, and so forth. Examples of such strains include *Escherichia coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (refer to Japanese Patent Laid-open (Kokai) No. 56-106598).

L-Citrulline-Producing Bacteria

Examples of L-citrulline-producing bacteria and parental strains which can be used to derive L-citrulline-producing bacteria include, but are not limited to, strains belonging to the genus *Escherichia* such as *Escherichia coli* strains 237/pMADS11, 237/pMADS12, and 237/pMADS13 (RU2215783 C2, European Patent No. 1170361 B1, U.S. Pat. No. 6,790,647 B2), which harbor mutant N-acetylglutamate synthase, *Escherichia coli* strains 333 (VKPM B-8084) and 374 (VKPM B-8086), both harboring mutant feedback-resistant carbamoyl phosphate synthetase (Russian Patent No. 2264459 C2), *Escherichia coli* strains in which α-ketoglutarate synthase activity is increased, and ferredoxin NADP$^+$ reductase, pyruvate synthase, and/or α-ketoglutarate dehydrogenase activities are additionally modified (EP2133417 A1), and *Pantoea ananantis* strain NA1sucAsdhA, in which succinate dehydrogenase and α-ketoglutarate dehydrogenase activities are decreased (U.S. Patent Application No. 2009286290 A1), and the like.

As L-citrulline is an intermediate in the L-arginine biosynthetic pathway, examples of L-citrulline-producing bacteria and parent strains which can be used to derive L-citrulline-producing bacteria, include strains in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argq, acetylornithine transaminase (argD), acetylornithine deacetylase (argE), ornithine carbamoyltransferase (argF/I), and carbamoyl phosphate synthetase (carAB), and combinations thereof.

An L-citrulline-producing bacterium can be also easily obtained from any L-arginine-producing bacterium, for example *Escherichia coli* 382 stain (VKPM B-7926), by inactivation of argininosuccinate synthase encoded by argG gene.

L-Cysteine-Producing Bacteria

Examples of L-cysteine-producing bacteria and parental strains which can be used to derive L-cysteine-producing bacteria include, but are not limited to, strains belonging to the genus *Escherichia* such as *Escherichia coli* JM15 transformed with different cysE alleles encoding feedback-resistant serine acetyltransferases (U.S. Pat. No. 6,218,168 B1, Russian Patent No. 2279477 C2), *Escherichia coli* W3110 having overexpressed genes which encode proteins suitable for secreting substances toxic for cells (U.S. Pat. No. 5,972,663 A), *Escherichia coli* strains having a lowered cysteine desulfohydrase activity (JP11155571 A2), *Escherichia coli* W3110 having an increased activity of a positive transcriptional regulator for cysteine regulon encoded by the cysB gene (WO0127307 A1), and the like. Examples of L-cysteine-producing bacteria and parental strains which can be used to derive L-cysteine-producing bacteria also include *E. coli* strain JM15(ydeD), which is a derivative of *E. coli* JM15 (U.S. Pat. No. 6,218,168 B1), and has been transformed with DNA containing the ydeD gene (U.S. Pat. No. 5,972,663).

L-Glutamic Acid-Producing Bacteria

Examples of L-glutamic acid-producing bacteria and parental strains which can be used to derive L-glutamic acid-producing bacteria include, but are not limited to, strains belonging to the genus *Escherichia* such as *Escherichia coli* VL334thrC$^+$ (EP 1172433 A1). The *Escherichia coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *Escherichia coli* strain K-12 (VKPM B-7) cells. As a result, an L-isoleucine auxotrophic strain VL334thrC$^+$ (VKPM B-8961), which is able to produce L-glutamic acid, was obtained.

Examples of L-glutamic acid-producing bacteria and parental strains which can be used to derive the L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltBD), isocitrate dehydrogenase (icdA), aconitate hydratase (acnA, acnB), citrate synthase (gltA), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2.

Examples of L-glutamic acid-producing bacteria and parental strains which can be used to derive the L-glutamic acid-producing bacteria also include strains having a decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), acetolactate synthase (ilvI), formate acetyltransferase (pfl), lactate dehydrogenase (ldh), glutamate decarboxylase (gadAB), and succinate dehydrogenase (sdhABCD). Shown in the parentheses after the names of the enzymes are the genes encoding the enzymes (the same shall apply to the same occasions hereafter). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*Escherichia coli* W3110sucA::Km$^R$,
*Escherichia coli* AJ12624 (FERM BP-3853),
*Escherichia coli* AJ12628 (FERM BP-3854),
*Escherichia coli* AJ12949 (FERM BP-4881).

*Escherichia coli* W3110sucA::Km$^R$ is a strain obtained by disrupting the α-ketoglutarate dehydrogenase gene (hereinafter referred to as "sucA gene") of *Escherichia coli* W3110. This strain is completely deficient in the α-ketoglutarate dehydrogenase.

Other examples of L-glutamic acid-producing bacteria and parental strains which can be used to derive the L-glutamic acid-producing bacteria include strains that belong to the genus *Escherichia* and have resistance to an aspartic acid antimetabolite (aspartic acid analogue). These strains can also be deficient in the α-ketoglutarate dehydrogenase activity and examples thereof include, for example, *Escherichia coli* AJ13199 (FERM BP-5807) (U.S. Pat. No. 5,908,768), *Escherichia coli* FFRM P-12379, which additionally has a lowered L-glutamic acid-decomposing ability (U.S. Pat. No. 5,393,671), *Escherichia coli* AJ13138 (FERM BP-5565) (U.S. Pat. No. 6,110,714), and the like.

Examples of L-glutamic acid-producing bacteria and parental strains which can be used to derive the L-glutamic acid-producing bacteria also include *Pantoea* bacteria, such as the *Pantoea ananatis* AJ13355 strain (FERM BP-6614), *Pantoea ananatis* SC17 strain (FERM BP-11091), and *Pantoea ananatis* SC17(0) strain (VKPM B-9246). The AJ13355 strain is a strain isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depositary (currently, independent administrative agency, National Institute of Technology and Evaluation, International Patent Organism Depositary (NITE IPOD), #120, 2-5-8 Kazusakamatari, Kisarazu-shi, Chiba, 292-0818, Japan) on Feb. 4, 2009, and assigned an accession number of FERM BP-11091. The AJ13355 strain was deposited at the National Institute of Bioscience and Human Technology, Agency of Industrial Science and Technology, Ministry of International Trade and Industry (currently, NITE IPOD), #120, 2-5-8 Kazusakamatari, Kisarazu-shi, Chiba, 292-0818, Japan) on Feb. 19, 1998 and assigned an accession number of FERM P-16644. Then, the deposit was converted to an international deposit under the provisions of the Budapest Treaty on Jan. 11, 1999, and assigned an accession number of FERM BP-6614.

Examples of L-glutamic acid-producing bacteria and parental strains which can be used to derive the L-glutamic acid-producing bacteria also include mutant strains belonging to the genus *Pantoea* that are deficient in the α-ketoglutarate dehydrogenase activity or have a decreased α-ketoglutarate dehydrogenase activity, and can be obtained as described above. Such strains include *Pantoea ananatis* AJ13356 (U.S. Pat. No. 6,331,419 B1). *Pantoea ananatis* AJ13356 was deposited at the National Institute of Bioscience and Human-Technology, Agency of Industrial Science and Technology, Ministry of International Trade and Industry (currently, NITE IPOD, #120, 2-5-8 Kazusakamatari, Kisarazu-shi, Chiba, 292-0818, Japan) on Feb. 19, 1998 under the accession number FERM P-16645. It was then converted to an international deposit under the provisions of the Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

Examples of L-glutamic acid-producing bacteria and parental strains which can be used to derive the L-glutamic acid-producing bacteria also include strains belonging to the genus *Pantoea* such as the *Pantoea ananatis* SC17sucA/RSFCPG+pSTVCB strain, *Pantoea ananatis* AJ13601 strain, *Pantoea ananatis* NP106 strain, and *Pantoea ananatis* NA1 strain. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from *Escherichia coli*, and the plasmid pSTVCB containing the citrate synthase gene (gltA) derived from *Brevibacterium lactofetmentum*, into the SC17sucA strain. The AJ13601 strain is a strain selected from the SC17sucA/RSFCPG+pSTVCB strain as a strain resistant to a high concentration of L-glutamic acid at a low pH. The NP106 strain was obtained from the AJ13601 strain by curing the RSFCPG and pSTVCB plasmids. The AJ13601 strain was deposited at the National Institute of Bioscience and Human Technology, Agency of Industrial Science and Technology, Ministry of International Trade and Industry (currently, NITE IPOD, #120, 2-5-8 Kazusakamatari, Kisarazu-shi, Chiba, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

L-Histidine-Producing Bacteria

Examples of L-histidine-producing bacteria and parental strains which can be used to derive L-histidine-producing bacteria include, but are not limited to, strains belonging to the genus *Escherichia* such as *Escherichia coli* strain 24 (VKPM B-5945, RU2003677 C1), *Escherichia coli* strain 80 (VKPM B-7270, RU2119536 C1), *Escherichia coli* NRRL B-12116-B-12121 (U.S. Pat. No. 4,388,405), *Escherichia coli* H-9342 (FERM BP-6675) and H-9343 (FERM BP-6676) (U.S. Pat. No. 6,344,347 B1), *Escherichia coli* H-9341 (FERM BP-6674) (EP1085087 A2), *Escherichia coli* AI80/pFM201 (U.S. Pat. No. 6,258,554 B1), and the like.

Examples of L-histidine-producing bacteria and parental strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl-AMP cyclohydrolase (hisI), phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 C1 and 2119536 C1).

Specific examples of strains having an L-histidine-producing ability include *Escherichia coli* FERM-P 5038 and 5048, which have been transformed with a vector carrying a DNA encoding an L-histidine-biosynthetic enzyme (JP 56-005099 A), *Escherichia coli* strains transformed with rht, a gene for an amino acid-export (EP1016710 A2), *Escherichia coli* 80 strain, which has been imparted with sulfaguanidine, DL-1,2,4-triazole-3-alanine, and streptomycinresistance (VKPM B-7270, RU2119536 C1), *Escherichia coli* MG1655+hisGr hisL'_Δ ΔpurR (RU2119536 and Doroshenko V. G. et al., The directed modification of *Escherichia coli* MG1655 to obtain histidine-producing mutants, *Prikl. Biochim. Mikrobiol.* (*Russian*), 2013, 49(2):149-154), and so forth.

L-Isoleucine-Producing Bacteria

Examples of L-isoleucine-producing bacteria and parental strains which can be used to derive L-isoleucine-producing bacteria include, but are not limited to, mutant strains having resistance to 6-dimethylaminopurine (JP 5-304969 A), mutant strains having resistance to an isoleucine analogue such as thiaisoleucine and isoleucine hydroxamate, and mutant strains additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as L-isoleucine-producing bacteria or parental strains thereof (JP 2-458 A, EP0356739 A1, and U.S. Pat. No. 5,998,178).

L-Leucine-Producing Bacteria

Examples of L-leucine-producing bacteria and parental strains which can be used to derive L-leucine-producing bacteria include, but are not limited to, strains belonging to the genus *Escherichia* such as *Escherichia coli* strains resistant to leucine (for example, the strain 57 (VKPM B-7386, U.S. Pat. No. 6,124,121)); *Escherichia coli* strains resistant to leucine analogs including β-2-thienylalanine, 3-hydroxyleucine, 4-azaleucine, 5,5,5-trifluoroleucine (JP 62-34397 B and JP 8-70879 A); *Escherichia coli* strains obtained by the gene engineering method described in WO96/06926; *Escherichia coli* H-9068 (JP 8-70879 A), and the like.

Examples of L-leucine-producing bacteria and parental strains which can be used to derive L-leucine-producing bacteria also include strains in which the expression of one or more genes involved in L-leucine biosynthesis is enhanced. Examples of such genes include genes of the leuABCD operon, which can be represented by a mutant leuA gene encoding α-isopropylmalate synthase freed from feedback inhibition by L-leucine (U.S. Pat. No. 6,403,342 B1). In addition, examples of L-leucine-producing bacteria and parental strains which can be used to derive L-leucine-producing bacteria also include strains in which the expression of one or more genes encoding proteins which excrete L-amino acid from the bacterial cell is enhanced. Examples of such genes include the b2682 and b2683 genes (ygaZH genes) (EP1239041 A2).

L-Lysine-Producing Bacteria

Examples of L-lysine-producing bacteria and parental strains which can be used to derive L-lysine-producing bacteria include mutant strains belonging to the genus *Escherichia* and having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these strains, feedback inhibition of aspartokinase by L-lysine is desensitized.

Examples of L-lysine-producing bacteria and parental strains which can be used to derive L-lysine-producing bacteria also include strains in which expression of one or more genes encoding an L-lysine biosynthetic enzyme is enhanced. Examples of such genes include, but are not limited to, genes encoding dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), and aspartase (aspA) (EP1253195 A1). In addition, the L-lysine-producing bacteria or parental strains thereof may have an increased level of expression of the gene involved in energy efficiency (cyo) (EP1170376 A1), the gene encoding nicotinamide nucleotide transhydrogenase (pntAB) (U.S. Pat. No. 5,830,716 A), the ybjE gene (WO2005/073390), or combinations thereof. Since aspartokinase III is subject to feedback inhibition by L-lysine, a mutant lysC gene coding for an aspartokinase III desensitized to feedback inhibition by L-lysine (U.S. Pat. No. 5,932,453) may be used for enhancing the activity of this enzyme. Further, since dihydrodipicolinate synthase is subject to feedback inhibition by L-lysine, a mutant dapA gene coding for a dihydrodipicolinate synthase desensitized to feedback inhibition by L-lysine may be used for enhancing the activity of this enzyme.

L-Lysine-producing bacteria or parental strains which can be used to derive L-lysine-producing bacteria may have a reduced or no activity of an enzyme that catalyzes a reaction which causes a branching off from the L-lysine biosynthesis pathway and results in the production of another compound. Also, L-lysine-producing bacteria or parental strains which can be used to derive L-lysine-producing bacteria may have a reduced or no activity of an enzyme that negatively acts on L-lysine synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

Examples of L-lysine-producing bacteria and parental strains which can be used to derive L-lysine-producing bacteria also include the *Escherichia coli* WC196 strain (U.S. Pat. No. 5,827,698), the *Escherichia coli* WC196ΔcadAΔldc strain, and the *Escherichia coli* WC196ΔcadAΔldcC/pCABD2 strain (WO2006/078039).

The WC196 strain was bred from the W3110 strain, which was derived from *Escherichia coli* K-12, by conferring AEC resistance to the W3110 strain (U.S. Pat. No. 5,827,698). The WC196 strain was designated *Escherichia coli* AJ13069, deposited at the National Institute of Bioscience and Human-Technology, Agency of Industrial Science and Technology (currently, NITE IPOD, #120, 2-5-8 Kazusakamatari, Kisarazu-shi, Chiba, 292-0818, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

The WC196ΔcadAΔldc strain was constructed from the WC196 strain by disrupting the cadA and ldcC genes which encode lysine decarboxylase. The WC196ΔcadAΔldcC was designated AJ110692 and deposited at the independent administrative agency, National Institute of Advanced Industrial Science and Technology, International Patent Organism Depositary (currently, NITE IPOD, #120, 2-5-8 Kazusakamatari, Kisarazu-shi, Chiba, 292-0818, Japan) on Oct. 7, 2008 as an international deposit under the accession number FERM BP-11027.

The WC196ΔcadAΔldcC/pCABD2 strain was constructed by introducing the plasmid pCABD2 containing lysine biosynthesis genes (U.S. Pat. No. 6,040,160) into the WC196ΔcadAΔldcC strain. The plasmid pCABD2 contains a mutant dapA gene derived from *Escherichia coli* and coding for a dihydrodipicolinate synthase (DDPS) having a mutation for desensitization to feedback inhibition by L-lysine (H118Y), a mutant lysC gene derived from *Escherichia coli* and coding for aspartokinase III having a mutation for desensitization to feedback inhibition by L-lysine (T352I), the dapB gene derived from *Escherichia coli* and coding for dihydrodipicolinate reductase, and the ddh gene derived from *Brevibacterium lactofermentum* and coding for diaminopimelate dehydrogenase.

Examples of L-lysine-producing bacteria and parental strains which can be used to derive L-lysine-producing bacteria also include *Escherichia coli* AJIK01 (NITE BP-01520). The AJIK01 strain was designated *Escherichia coli* AJ111046, and deposited at NITE IPOD (#120, 2-5-8 Kazusakamatari, Kisarazu-shi, Chiba, 292-0818, Japan) on Jan. 29, 2013. Then, it was converted to an international deposit under the provisions of the Budapest Treaty on May 15, 2014, and assigned an accession number of NITE BP-01520.

L-Methionine-Producing Bacteria

Examples of L-methionine-producing bacteria and parent strains which can be used to derive L-methionine-producing bacteria include, but are not limited to, strains belonging to the genus *Escherichia* such as *Escherichia coli* strains AJ11539 (NRRL B-12399), AJ11540 (NRRL B-12400), AJ11541 (NRRL B-12401), AJ 11542 (NRRL B-12402) (Patent GB2075055); and *Escherichia coli* strains 218 (VKPM B-8125) (RU2209248 C2) and 73 (VKPM B-8126) (RU2215782 C2) resistant to norleucine, the L-methionine analog, or the like. The strain *Escherichia coli* 73 was deposited in the Russian National Collection of Industrial Microorganisms (VKPM; FGUP GosNII Genetika, Russian Federation, 117545 Moscow, $1^{st}$ Dorozhny proezd, 1) on May 14, 2001 under the accession number VKPM B-8126. Then, it was converted to an international deposit under the provisions of the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as L-methionine-producing bacteria or parent strains thereof.

L-Ornithine-Producing Bacteria

As L-ornithine is an intermediate of L-arginine biosynthetic pathway, examples of L-ornithine-producing bacteria and parent strains which can be used to derive L-ornithine-producing bacteria, include strains in which expression of one or more genes encoding an L-arginine biosynthetic enzyme, such as those described above, is enhanced.

An L-ornithine-producing bacterium can be easily obtained from any L-arginine-producing bacterium, for example *Escherichia coli* 382 strain (VKPM B-7926), by inactivation of ornithine carbamoyltransferase encoded by both argF and argI genes. Methods for inactivation of ornithine carbamoyltransferase are described herein.

L-Phenylalanine-Producing Bacteria

Examples of L-phenylalanine-producing bacteria and parental strains which can be used to derive L-phenylalanine-producing bacteria include, but are not limited to, strains belonging to the genus *Escherichia* such as *Escherichia coli* AJ12739 (tyrA::Tn10, tyrR) (VKPM B-8197), *Escherichia coli* HW1089 (ATCC 55371) harboring the mutant pheA34 gene (U.S. Pat. No. 5,354,672), *Escherichia coli* MWEC101-b (KR8903681), *Escherichia coli* NRRL B-12141, NRRL B-12145, NRRL B-12146, and NRRL B-12147 (U.S. Pat. No. 4,407,952), *Escherichia coli* K-12 (W3110 (tyrA)/pPHAB (FERM BP-3566)), *Escherichia coli* K-12 (W3110 (tyrA)/pPHAD (FERM BP-12659)), *Escherichia coli* K-12 (W3110 (tyrA)/pPHATerm (FERM BP-12662)), and *Escherichia coli* K-12 (W3110 (tyrA)/pBR-aroG4, pACMAB) named as AJ12604 (FERM BP-3579) (EP488424 B1). Furthermore, L-phenylalanine-producing bacteria and parental strains which can be used to derive L-phenylalanine-producing bacteria also include strains belonging to the genus *Escherichia* and having an enhanced activity of the protein encoded by the yedA gene or the yddG gene (U.S. Pat. Nos. 7,259,003 and 7,666,655).

L-Proline-Producing Bacteria

Examples of L-proline-producing bacteria and parental strains which can be used to derive L-proline-producing bacteria include, but are not limited to, strains belonging to the genus *Escherichia* such as *Escherichia coli* 702ilvA (VKPM B-8012), which is deficient in the ilvA gene and is able to produce L-proline (EP1172433 A1). Examples of L-proline-producing bacteria and parental strains which can be used to derive L-proline-producing bacteria also include strains in which the expression of one or more genes involved in L-proline biosynthesis is enhanced. Examples of such genes which can be used in L-proline-producing bacteria include the proB gene encoding glutamate kinase with desensitized feedback inhibition by L-proline (DE3127361 A1). In addition, examples of L-proline-producing bacteria and parental strains which can be used to derive L-proline-producing bacteria also include strains in which the expression of one or more genes encoding proteins responsible for excreting L-amino acid from the bacterial cell is enhanced. Examples of such genes include the b2682 and b2683 genes (ygaZH genes) (EP1239041 A2).

Examples of bacteria belonging to the genus *Escherichia* that have an ability to produce L-proline include the following *Escherichia coli* strains: NRRL B-12403 and NRRL B-12404 (GB Patent 2075056), VKPM B-8012 (Russian Patent No. 2207371 C2), plasmid mutants described in DE3127361 A1, plasmid mutants described by Bloom F. R. et al. in "The 15th Miami winter symposium", 1983, p. 34, and the like.

L-Threonine-Producing Bacteria

Examples of L-threonine-producing bacteria and parental strains which can be used to derive L-threonine-producing bacteria include, but are not limited to, strains belonging to the genus *Escherichia* such as *Escherichia coli* TDH-6/pVIC40 (VKPM B-3996) (U.S. Pat. Nos. 5,175,107 and 5,705,371), *Escherichia coli* 472T23/pYN7 (ATCC 98081) (U.S. Pat. No. 5,631,157), *Escherichia coli* NRRL B-21593 (U.S. Pat. No. 5,939,307), *Escherichia coli* FERM BP-3756 (U.S. Pat. No. 5,474,918), *Escherichia coli* FERM BP-3519 and FERM BP-3520 (U.S. Pat. No. 5,376,538), *Escherichia coli* MG442 (Gusyatiner M. et al., Genetika (Russian), 1978, 14:947-956), *Escherichia coli* VL643 and VL2055 (EP1149911 A2), *Escherichia coli* VKPM B-5318 (EP0593792 A1), and the like.

The strain TDH-6 is deficient in the thrC gene, as well as being sucrose-assimilative, and the ilvA gene thereof has a leaky mutation. This strain also has a mutation in the rhtA gene, which mutation imparts resistance to high concentrations of threonine or homoserine. The strain VKPM B-3996, which contains the plasmid pVIC40, was obtained by introducing the plasmid pVIC40 into the TDH-6 strain. The plasmid pVIC40 was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain VKPM B-3996 was deposited on Nov. 19, 1987 in the All-Union Scientific Center of Antibiotics (Russian Federation, 117105 Moscow, Nagatinskaya Street 3-A) under the accession number RIA 1867. The strain VKPM B-3996 was also deposited in the Russian National Collection of Industrial Microorganisms (VKPM; FGUP GosNII Genetika, Russian Federation, 117545 Moscow, 1st Dorozhny proezd, 1) on Apr. 7, 1987 under the accession number VKPM B-3996.

The strain B-5318 is prototrophic with regard to isoleucine; and harbors the plasmid pPRT614, which corresponds to the plasmid pVIC40 of which the regulatory region of the threonine operon is replaced with a temperature-sensitive lambda-phage C1 repressor and PR promoter. The strain VKPM B-5318 was deposited in the Russian National Collection of Industrial Microorganisms (VKPM) on May 3, 1990 under the accession number VKPM B-5318.

L-Threonine-producing bacteria or parental strains which can be used to derive L-threonine-producing bacteria can be modified to enhance expression of one or more of the following genes:

the mutant thrA gene which encodes aspartokinase homoserine dehydrogenase I resistant to feedback inhibition by threonine, the thrB gene which encodes homoserine kinase, the thrC gene which encodes threonine synthase, the rhtA gene which encodes a putative transmembrane protein of the threonine and homoserine efflux system, the asd gene which encodes aspartate-β-semialdehyde dehydrogenase, and the aspC gene which encodes aspartate aminotransferase (aspartate transaminase).

The thrA gene which encodes aspartokinase I and homoserine dehydrogenase I of *Escherichia coli* has been elucidated (KEGG, Kyoto Encyclopedia of Genes and Genomes, entry No. b0002; GenBank, accession No. NC_000913.2; nucleotide positions: 337 to 2,799; Gene ID: 945803). The thrA gene is located between the thrL and thrB genes on the chromosome of *Escherichia coli* K-12.

The thrB gene which encodes homoserine kinase of *Escherichia coli* has been elucidated (KEGG, entry No. b0003; GenBank, accession No. NC_000913.2; nucleotide positions: 2,801 to 3,733; Gene ID: 947498). The thrB gene is located between the thrA and thrC genes on the chromosome of *Escherichia coli* K-12.

The thrC gene which encodes threonine synthase of *Escherichia coli* has been elucidated (KEGG, entry No. b0004; GenBank, accession No. NC_000913.2; nucleotide positions: 3,734 to 5,020; Gene ID: 945198). The thrC gene is located between the thrB and yaaX genes on the chromosome of *Escherichia coli* K-12. All three genes function as a single threonine operon thrABC. To enhance expression of the threonine operon, the attenuator region which affects the transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *Escherichia coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *Escherichia coli* has been elucidated (KEGG, entry No. b0813; GenBank, accession No. NC_000913.2; nucleotide positions: 848,433 to 849,320, complement; Gene ID: 947045). The rhtA gene is located between the dps and ompX genes on the chromosome of *Escherichia coli* K-12 close to the glnHPQ operon, which encodes components of the glutamine transport system. The rhtA gene is identical to the ybiF gene (KEGG, entry No. b0813).

The asd gene which encodes aspartate-β-semialdehyde dehydrogenase of *Escherichia coli* has been elucidated (KEGG, entry No. b3433; GenBank, accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *Escherichia coli* K-12.

Also, the aspC gene which encodes aspartate aminotransferase of *Escherichia coli* has been elucidated (KEGG, entry No. b0928; GenBank, accession No. NC_000913.2; nucleotide positions: 983,742 to 984,932, complement; Gene ID: 945553). The aspC gene is located between the ycbL gene on the opposite strand and the ompF gene on the same strand on the chromosome of *Escherichia coli* K-12.

L-Tryptophan-Producing Bacteria

Examples of L-tryptophan-producing bacteria and parental strains which can be used to derive the L-tryptophan-producing bacteria include, but are not limited to, strains belonging to the genus *Escherichia* such as *Escherichia coli* JP4735/pMU3028 (DSM10122) and JP6015/pMU91 (DSM10123) which have a mutant trpS gene encoding a partially inactivated tryptophanyl-tRNA synthetase (U.S. Pat. No. 5,756,345), *Escherichia coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373 B1), *Escherichia coli* AGX17 (pGX44) (NRRL B-12263) and AGX6(pGX50) aroP (NRRL B-12264) deficient in the enzyme tryptophanase (U.S. Pat. No. 4,371,614), *Escherichia coli* AGX17/pGX50,pACKG4-pps having an enhanced phosphoenolpyruvate-producing ability (WO97/08333, U.S. Pat. No. 6,319,696 B1), and the like. Examples of L-tryptophan-producing bacteria and parental strains which can be used to derive the L-tryptophan-producing bacteria also include strains belonging to the genus *Escherichia* and having an enhanced activity of the protein encoded by and the yedA gene or the yddG gene (U.S. Patent Application Nos. 2003148473 A1 and 2003157667 A1).

Examples of L-tryptophan-producing bacteria and parental strains which can be used to derive the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, and hence, a mutation desensitizing the feedback inhibition may be introduced into these enzymes. Specific examples of strains having such a mutation include *Escherichia coli* SV164, which harbors desensitized anthranilate synthase, and a transformant strain obtained by introducing into the *Escherichia coli* SV164 the plasmid pGH5 (WO94/08031 A1), which contains a mutant serA gene encoding feedback-desensitized phosphoglycerate dehydrogenase.

Examples of L-tryptophan-producing bacteria and parental strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Valine-Producing Bacteria

Examples of L-valine-producing bacteria and parental strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon can be disrupted so that threonine deaminase activity is decreased.

Examples of L-valine-producing bacteria and parental strains for deriving L-valine-producing bacteria also include mutant strains having a mutation in aminoacyl-tRNA synthetase (U.S. Pat. No. 5,658,766). Examples of such strains include *Escherichia coli* VL1970, which has a mutation in the ileS gene encoding isoleucine tRNA synthetase. *Escherichia coli* VL1970 was deposited in the Russian National Collection of Industrial Microorganisms (VKPM; FGUP GosNII Genetika, Russian Federation, 117545 Moscow, 1$^{st}$ Dorozhny proezd, 1) on Jun. 24, 1988 under the accession number VKPM B-4411.

Furthermore, mutant strains requiring lipoic acid for growth and/or lacking H$^+$-ATPase can also be used as L-valine-producing bacteria or parental strains thereof (WO96/06926 A1).

Examples of L-valine-producing bacteria and parent strains for deriving L-valine-producing bacteria also include *Escherichia coli* H81 strain (VKPM B-8066; see, for example, EP1942183 B1), *Escherichia coli* NRRL B-12287 and NRRL B-12288 (U.S. Pat. No. 4,391,907), *Escherichia coli* VKPM B-4411 (U.S. Pat. No. 5,658,766), *Escherichia coli* VKPM B-7707 (EP1016710 A2), or the like.

The bacterium as described herein belonging to the family Enterobacteriaceae has been modified to overexpress a gene encoding an iron exporter.

The phrase "a gene encoding an iron exporter" can mean a gene which encodes a protein having an activity of exporting iron. Similarly, the phrase "an iron exporter" can mean a protein having an activity of exporting iron. The iron exporter is also referred to as "iron ions exporter" or "ferrous exporter". That is, the phrases "iron exporter", "iron ions exporter", and "ferrous exporter" may be used equivalently, and they are within the knowledge of the one skilled in the art.

Specific examples of the gene encoding an iron exporter include the fetB gene, the fetA gene, and the fieF gene. Particular examples of the gene encoding an iron exporter include the fetB gene and the fieF gene. The bacterium may be modified to overexpress one gene encoding an iron exporter or two or more genes encoding an iron exporter. Hence, specific examples of the gene encoding an iron exporter also include combinations of the fetB, fetA, and fieF genes, i.e. combinations of any two of them or all of them. A specific example of the combination include a combination of the fetB and fetA genes, as these genes encode proteins FetB and FetA, respectively, which constitute the FetAB complex that functions as an iron exporter. The more specific description of the fetB, fetA, and fieF genes, and proteins encoded thereby is given hereinafter.

The fetB gene (synonym: ybbM) encodes membrane unit FetB of the ABC-type transporter FetAB (synonym: iron exporter permease subunit) (KEGG, Kyoto Encyclopedia of Genes and Genomes, entry No. b0491; Protein Knowledgebase, UniProtKB/Swiss-Prot, accession No. P77307). The fetB gene (GenBank, accession No. NC_000913.3; nucleotide positions: 516583 to 517362; Gene ID: 945137) is located between the fetA gene and the ybbN gene on the same strand on the chromosome of *Escherichia coli* strain K-12. The nucleotide sequence of the fetB gene (SEQ ID NO: 1) of *Escherichia coli* strain K-12 and the amino acid sequence of the FetB protein (SEQ ID NO: 2) encoded by the fetB gene of *Escherichia coli* strain K-12 are known.

The fetA gene (synonym: ybbL) encodes the ATP-binding subunit FetA of the ABC-type transporter FetAB (KEGG, entry No. b0490; Protein Knowledgebase, UniProtKB/Swiss-Prot, accession No. P77279). The fetA gene (GenBank, accession No. NC_000913.3; nucleotide positions: 515919 to 516596; Gene ID: 946990) is located between the qmcA gene on the opposite strand and the fetB gene on the same strand on the chromosome of *Escherichia coli* strain K-12. The nucleotide sequence of the fetA gene (SEQ ID NO: 3) of *Escherichia coli* strain K-12 and the amino acid sequence of the FetA protein (SEQ ID NO: 4) encoded by the fetA gene of *Escherichia coli* strain K-12 are known.

The fieF gene (synonym: yiiP) encodes metal ions ($Zn^{2+}$/$Fe^{2+}$/$Cd^{2+}$) efflux transporter FieF (synonym: ferrous-iron efflux pump) (KEGG, entry No. b3915; Protein Knowledgebase, UniProtKB/Swiss-Prot, accession No. P69380). The fieF gene (GenBank, accession No. NC_000913.3; nucleotide positions: 4106469 to 4107371; Gene ID: 948413) is located between the cpxP gene and the pfkA gene on the same strand on the chromosome of *Escherichia coli* strain K-12. The nucleotide sequence of the fieF gene (SEQ ID NO: 5) of *Escherichia coli* strain K-12 and the amino acid sequence of the FieF protein (SEQ ID NO: 6) encoded by the fieF gene of *Escherichia coli* strain K-12 are known.

That is, the gene encoding an iron exporter may have the nucleotide sequence of SEQ ID NO: 1, 3, or 5, and the iron exporter may have the amino acid sequence of SEQ ID NO: 2, 4, or 6. The phrase "a gene or protein has a nucleotide or amino acid sequence" encompasses cases where a gene or protein comprises the nucleotide or amino acid sequence, and cases where a gene or protein consists of the nucleotide or amino acid sequence.

As the FetB, FetA, and FieF proteins represent examples of the iron exporter as described herein, the explanations given herein or hereinafter for these proteins may be applied mutatis mutandis to other iron exporters. Further, as the fetB, fetA, and fieF genes represent examples of the gene encoding an iron exporter as described herein, the explanations given herein or hereinafter for these genes may be applied mutatis mutandis to other genes encoding an iron exporter.

The phrase "a bacterium has been modified to overexpress a gene encoding an iron exporter" can mean that the bacterium has been modified in such a way that in the modified bacterium the total activity of an iron exporter, i.e. the total activity of a protein encoded by a gene encoding an iron exporter, such as the FetB, FetA, or FieF protein, is increased as compared with, or the expression level (expression amount) of a gene encoding an iron exporter is higher than that level in, a non-modified strain, for example, a wild-type or parental strain as described above and hereinafter. Examples of a non-modified strain serving as a reference for the above comparison can include wild-type strains of bacteria belonging to the genus *Escherichia* such as the *Escherichia coli* MG1655 strain (ATCC 47076) and W3110 strain (ATCC 27325), wild-type strains of bacteria belonging to the genus *Pantoea* such as the *Pantoea ananatis* AJ13355 strain (FERM BP-6614), and so forth.

The phrase "a gene encoding an iron exporter is overexpressed" can mean that the total activity of an iron exporter, i.e. the total activity of a protein encoded by a gene encoding an iron exporter, such as the FetB, FetA, or FieF protein, is increased as compared with a non-modified strain. The total activity of an iron exporter can be increased by, for example, increasing (enhancing) the expression level of a gene encoding the iron exporter, or increasing the activity per molecule (may be referred to as a specific activity) of the protein encoded by the gene, as compared with a non-modified strain. The bacterium can be modified so that the activity of an iron exporter, such as the FetB, FetA, or FieF protein, per cell is increased to 150% or more, 200% or more, or 300% or more, of the activity of a non-modified strain.

The phrase "an activity of iron exporter" can also be referred to as "iron exporter activity". The phrase "an activity of iron exporter" can mean the activity of exporting iron ions by a bacterium belonging to the family Enterobacteriaceae. The phrase "an activity of iron exporter" can also mean the activity of transporting iron ions by a bacterium belonging to the family Enterobacteriaceae from cells of the bacterium into an outside medium through the cellular membrane. The phrase "an activity of iron exporter" can also mean the activity of exporting iron ions by a bacterium belonging to the family Enterobacteriaceae utilizing one or more proteins capable of transporting iron ions from cells of the bacterium into an outside medium through the cellular membrane. The phrase "an activity of iron exporter" can also mean the activity of exporting iron ions by a bacterium belonging to the family Enterobacteriaceae utilizing one or more proteins having the amino acid sequence of SEQ ID NO: 2, 4 or 6. That is, specific examples of the activity of iron exporter include an activity of iron exporter having the amino acid sequence of SEQ ID NO: 2, 4, or 6. The iron exporter may have an activity of iron exporter solely or in combination of the other subunit(s). For example, the FieF protein may function as an iron exporter solely, and hence, the phrase "an activity of iron exporter" used for the FieF protein can mean such an activity of exporting iron ions as mentioned above solely. Meanwhile, the FetA and FetB proteins may constitute the FetAB complex to function as an iron exporter, and hence, the phrase "an activity of iron exporter" used for the FetA or FetB protein can mean such an activity of exporting iron ions as mentioned above in combination with the corresponding pair, i.e. the FetB protein for the FetA protein, or the FetA protein for the FetB protein. The phrases "exporter", "importer", "symporter", "antiporter", "uniporter", "efflux", "influx", "uptake", and so forth are within the knowledge of the one skilled in the art.

The phrase "an activity of iron exporter having the amino acid sequence of SEQ ID NO: 2" can mean the activity of a protein having the amino acid sequence of SEQ ID NO: 2, and can specifically mean the activity of exporting iron ions utilizing the protein having the amino acid sequence of SEQ ID NO: 2 from cells of a bacterium belonging to the family Enterobacteriaceae. It is also acceptable that the phrase "an activity of iron exporter having the amino acid sequence of SEQ ID NO: 2" can mean the activity of the FetB protein having the amino acid sequence of SEQ ID NO: 2, and can specifically mean the activity of exporting iron ions utilizing the FetB protein having the amino acid sequence of SEQ ID NO: 2 from cells of a bacterium belonging to the family Enterobacteriaceae. The explanations given herein for the phrase "an activity of iron exporter having the amino acid sequence of SEQ ID NO: 2" may be applied mutatis mutandis to the phrases "an activity of iron exporter having the amino acid sequence of SEQ ID NO: 4" and "an activity of iron exporter having the amino acid sequence of SEQ ID NO: 6", wherein the FetB protein should be read as the FetA protein and the FieF protein, respectively.

The "iron ions" can be exported in the reduced ferrous ($Fe^{2+}$) form or the oxidized ferric ($Fe^{3+}$) form, which forms may represent free iron ions or an adduct formed by one or more iron ions and another one or more organic or inorganic compound, such as water.

The activity of an iron exporter can be determined by evaluating the activity of exporting iron ions. The activity of an iron exporter can be determined particularly as a specific activity per unit weight, such as mg or µg, of the protein. For example, the activity of an iron exporter can be determined by evaluating the amount of intracellular free iron using electron paramagnetic resonance (EPR) spectroscopy (Nicolaou S. A. et al., *Appl. Environ. Microbiol.*, 2013, 79(23): 7210-7219; Woodmansee A. N. and Imlay J. A., Quantitation of intracellular free iron by electron paramagnetic resonance spectroscopy, *Methods Enzymol.*, 2002, 349:3-9). Alternatively, an approach based on fluorescence quenching in proteoliposomes can also be used to determine the activity of an iron exporter in vitro as described in Grass G. et al. (*Arch. Microbiol.*, 2005, 183:9-18). The protein concentration can be determined by the Bradford protein assay using bovine serum albumin as a standard (Bradford M. M., *Anal. Biochem.*, 1976, 72:248-254).

The phrase "a gene encoding an iron exporter is overexpressed" can also mean that the expression level (expression amount) of a gene encoding an iron exporter is higher than that level in a non-modified strain. Therefore, the phrase "a gene encoding an iron exporter is overexpressed" can be equivalent to the phrase "expression of a gene encoding an iron exporter is enhanced". The bacterium can be modified so that the expression amount of a gene encoding an iron exporter, such as the fetB, fetA, or fieF gene, per cell is increased to 150% or more, 200% or more, or 300% or more, of the activity of a non-modified strain.

Methods which can be used to enhance expression of a gene encoding an iron exporter include, but are not limited to, increasing the copy number of the gene, such as the copy number of the gene in the chromosome of the bacterium and/or in an autonomously replicating plasmid harbored by the bacterium. The copy number of a gene encoding an iron exporter can be increased by, for example, introducing the gene into the chromosome of the bacterium and/or introducing an autonomously replicating vector containing the gene into the bacterium.

Examples of the vectors include, but are not limited to, broad-host-range plasmids such as pMW118/119, pBR322, pUC19, and the like. A gene encoding an iron exporter can also be introduced into the chromosomal DNA of a bacterium by, for example, homologous recombination, Mu-driven integration, or the like. Only one copy, or two or more copies of a gene encoding an iron exporter may be introduced. For example, homologous recombination can be carried out using sequence with multiple copies in the chromosomal DNA to introduce multiple copies of a gene encoding an iron exporter into the chromosomal DNA. Sequences with multiple copies in the chromosomal DNA include, but are not limited to, repetitive DNA or inverted repeats present at the end of a transposable element. In addition, it is possible to incorporate a gene encoding an iron exporter into a transposon and allow it to be transferred to introduce multiple copies of the gene encoding an iron exporter into the chromosomal DNA. By using Mu-driven integration, more than 3 copies of the gene can be introduced into the chromosomal DNA during a single act (Akhverdyan V. Z. et al., *Biotechnol. (Russian)*, 2007, 3:3-20).

Further methods which can be used to enhance expression of a gene encoding an iron exporter include increasing the expression level of the gene by modification of expression regulatory region(s) of the gene. Expression regulatory region(s) of a gene encoding an iron exporter can be modified by, for example, replacing the native expression regulatory region(s) of the gene with native and/or modified foreign regulatory region(s). Expression regulatory region (s) can also be referred to as Expression regulatory sequence (s). As genes encoding an iron exporter may be organized in operon structure, the further method which can be used to enhance expression of a gene encoding an iron exporter includes increasing the expression level of an operon comprising the genes encoding an iron exporter by modification of expression regulatory region(s) of the operon. Expression regulatory region(s) of an operon containing genes encoding an iron exporter can be modified by, for example, replacing the native expression regulatory region(s) of the operon with native and/or modified foreign regulatory region(s). In this method, the expression of one or more genes encoding an iron exporter can be enhanced at the same time.

Expression regulatory regions can be exemplified by promoters, enhancers, attenuators and termination signals, anti-termination signals, ribosome-binding sites (RBS) and other expression control elements (e.g., regions to which repressors or inducers bind and/or binding sites for transcriptional and translational regulatory proteins, for example, in the transcribed mRNA). Such regulatory regions are described, for example, in Sambrook J., Fritsch E. F. and Maniatis T., "Molecular Cloning: A Laboratory Manual", $2^{nd}$ ed., Cold Spring Harbor Laboratory Press (1989). Modifications of regions controlling gene(s) expression can be combined with increasing the copy number of the gene(s) (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters suitable for enhancing expression of a gene encoding an iron exporter can be the potent promoters that are stronger than the native promoter of the gene encoding an iron exporter. For example, the lac promoter, the tip promoter, the trc promoter, the tac promoter, the $P_R$ or the $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of a gene encoding an iron exporter to obtain a stronger promoter function, thus resulting in the increased transcription level of the gene encoding an iron exporter located downstream of the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

The copy number, or the presence or absence of a gene, can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", 4th ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

There may be some differences in DNA sequences between the genera, species or strains of the family Enterobacteriaceae. Therefore, the genes encoding an iron exporter, such as the fetB, fetA, and fieF genes, are not limited to the genes shown in SEQ ID NOs: 1, 3 and 5, but may include genes which are variant nucleotide sequences of SEQ ID NOs: 1, 3, and 5, so long as the genes encode an iron exporter, such as the FetB, FetA, and FieF proteins, respectively. Similarly, the iron exporters, such as the FetB, FetA, and FieF proteins, are not limited to the proteins shown in SEQ ID NOs: 2, 4, and 6, but may include proteins which are variant proteins of SEQ ID NOs: 2, 4, and 6, so long as the proteins have an activity of iron exporter. Examples of such variant nucleotide sequences or variant proteins may include homologues of and artificially modified ones of these genes or proteins, such as homologues of and artificially modified ones of genes having the nucleotide sequences of SEQ ID NOs: 1, 3, and 5 or proteins having the amino acid sequences of SEQ ID NOs: 2, 4, and 6.

The phrase "a variant protein" can mean a protein which has one or more mutations in the sequence compared with the amino acid sequence of SEQ ID NO: 2, 4 or 6, whether they are substitutions, deletions, insertions, and/or additions of one or several amino acid residues, but which still maintains an activity or function similar to that of the FetB, FetA and FieF proteins, respectively, such as the activity of iron exporter as described above, or of which the three-dimensional structure is not significantly changed relative to the wild-type protein. The number of changes in the variant protein depends on the position in the three-dimensional structure of the protein or the type of amino acid residues. It can be, but is not strictly limited to, 1 to 50, in another example 1 to 30, in another example 1 to 15, in another example 1 to 10, and in another example 1 to 5, in SEQ ID NO: 2, 4 or 6. This is possible because some amino acids have high homology to one another, so that the activity or function of a protein is not affected by a change between such amino acids, or the three-dimensional structure of a protein is not significantly changed relative to the wild-type protein by a change between such amino acids. Therefore, the variant proteins encoded by a gene encoding an iron exporter may have an amino acid sequence having a homology, defined as the parameter "identity" when using the computer program BLAST, of not less than 50%, not less than 60%, not less than 70%, not less than 75%, not less than 80%, not less than 85%, not less than 90%, not less than 95%, not less than 98%, or not less than 99% with respect to the entire amino acid sequence shown in SEQ ID NO: 2, 4 or 6, as long as the activity or function of the iron exporter as described above is maintained, or the three-dimensional structure of the iron exporter as described above is not significantly changed relative to the wild-type protein.

The exemplary substitution, deletion, insertion, and/or addition of one or several amino acid residues can be a conservative mutation(s). The representative conservative mutation is a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that the activity or function similar to that of the FetB, FetA and FieF proteins, such as the activity of iron exporter as described above, is maintained, or the three-dimensional structure of the FetB, FetA and FieF proteins is not significantly changed relative to the wild-type protein.

To evaluate the degree of protein or DNA homology, several calculation methods can be used, such as BLAST search, FASTA search and ClustalW method. The BLAST (Basic Local Alignment Search Tool, ncbi.nlm.nih.gov/BLAST/) search is the heuristic search algorithm employed by the programs blastp, blastn, blastx, megablast, tblastn, and tblastx; these programs ascribe significance to their findings using the statistical methods of Karlin S. and Altschul S. F. ("Methods for assessing the statistical significance of molecular sequence features by using general scoring schemes" *Proc. Natl. Acad. Sci. USA,* 1990, 87:2264-2268; "Applications and statistics for multiple high-scoring segments in molecular sequences". *Proc. Natl. Acad. Sci. USA,* 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.,* 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.,* 1994, 22:4673-4680).

Examples of the iron exporter can include protein homologues of FetB, FetA and FieF. Examples of such protein homologues include those of various organisms such as bacteria of the family Enterobacteriaceae. For example, the protein homologues of FetB, FetA and FieF from different bacteria of the family Enterobacteriaceae are known (Nicolaou S. A. et al., 2013), that have the activity of iron exporter as described above. Examples of such protein homologues from bacteria of the family Enterobacteriaceae are described hereinafter (Tables 1-3) with indication of a homology value (as "identity", that is the identity of amino acid residues), taxonomy data, and accession and sequence record numbers of amino acid sequences in the NCBI database (National Center for Biotechnology Information, ncbi.nlm.nih.gov/protein/). While such protein homologues of FetB, FetA and FieF are examples of a wild-type iron exporter (a wild-type protein of an iron exporter), each of them may also correspond to a variant protein of another one, such as a variant protein of SEQ ID NO: 2, 4, or 6.

In addition, examples of the iron exporter can also include further variant proteins of such protein homologues of FetB, FetA and FieF. The explanations given herein for variant proteins of SEQ ID NO: 2, 4, or 6, e.g. that for mutations and sequence identity, can be applied mutatis mutandis to such further variant proteins.

The phrase "the FetB protein", "the FetA protein", or "the FieF protein" is not limited to the wild-type FetB, FetA, or FieF protein such as the FetB, FetA, or FieF protein shown in SEQ ID NO: 2, 4, or 6 and the protein homologues of FetB, FetA and FieF shown in Tables 1-3, but can correctively refer to the wild-type FetB, FetA, or FieF protein and respective variant proteins thereof.

TABLE 1

Protein homologues of FetB

| Identity | Organism | Accession No.*; Sequence record (GI) No.* |
|---|---|---|
| 100% | *Escherichia coli* str. K-12 substr. MG1655 | NP_415024.4; 90111141 |

TABLE 1-continued

Protein homologues of FetB

| Identity | Organism | Accession No.*; Sequence record (GI) No.* |
|---|---|---|
| 100% | *Shigella dysenteriae* 1012 | EDX35060.1; 194418976 |
| 90% | *Citrobacter* sp. KTE151 | WP_016152109.1; 507081359 |
| 99% | *Shigella flexneri* CDC 796-83 | EFW60594.1; 320185842 |
| 86% | *Klebsiella pneumoniae* | WP_043521432.1; 759825551 |
| 86% | *Enterobacter aerogenes* | WP_045393489.1; 779941880 |
| 88% | *Salmonella enterica* | WP_002948352.1; 489038014 |
| 86% | *Enterobacter cloacae* | WP_048966103.1; 895853418 |
| 67% | *Pantoea vagans* | WP_033735780.1; 727277611 |

*herein and after in Table 2 (Protein homologues of FetA) and Table 3 (Protein homologues of FieF)—in the NCBI database (National Center for Biotechnology Information, ncbi.nlm.nih.gov/)

TABLE 2

Protein homologues of FetA

| Identity | Organism | Accession No.; Sequence record (GI) No. |
|---|---|---|
| 100% | *Escherichia coli* str. K-12 substr. MG1655 | NP_415023.1; 16128474 |
| 100% | *Shigella sonnei* Ss046 | AAZ87255.1; 73854548 |
| 78% | *Citrobacter* (multispecies) | WP_003847509.1; 489944202 |
| 77% | *Enterobacter* sp. GN02600 | WP_047358027.1; 829878362 |
| 75% | *Salmonella enterica* | WP_000140185.1; 446062330 |
| 73% | *Klebsiella pneumoniae* | WP_040165811.1; 749529200 |
| 52% | *Pantoea ananatis* | WP_045140082.1; 770868445 |

TABLE 3

Protein homologues of FieF

| Identity | Organism | Accession No.; Sequence record (GI) No. |
|---|---|---|
| 100% | *Escherichia coli* str. K-12 substr. MG1655 | NP_418350.1; 16131753 |
| 100% | *Shigella dysenteriae* Sd197 | YP_405267.1; 82778918 |
| 100% | *Klebsiella pneumoniae* IS22 | CDK69829.1; 571216769 |
| 94% | *Citrobacter amalonaticus* | WP_046493396.1; 817120539 |
| 92% | *Salmonella enterica* | WP_001541240.1; 486186272 |
| 91% | *Enterobacter* sp. GN03164 | WP_047345514.1; 829777987 |
| 90% | *Kluyvera cryocrescens* | WP_052284215.1; 917770211 |
| 79% | *Pantoea vagans* | WP_033734480.1 GI:727276306 |
| 88% | *Enterobacter massiliensis* | WP_044185423.1; 763326976 |

Moreover, a gene encoding an iron exporter can be any gene, so long as it encodes an iron exporter. For example, a gene encoding an iron exporter can also be a variant nucleotide sequence, such as a variant nucleotide sequence of SEQ ID NO: 1, 3, or 5. The phrase "a variant nucleotide sequence" can mean a nucleotide sequence which encodes a variant protein of an iron exporter, or a nucleotide sequence which encodes a wild-type iron exporter using any synonymous amino acid codons according to the standard genetic code table (see, e.g., Lewin B., "Genes VIII", 2004, Pearson Education, Inc., Upper Saddle River, N.J. 07458). Therefore, a gene encoding an iron exporter can be a variant nucleotide sequence due to the degeneracy of the genetic code, such as a variant nucleotide sequence of SEQ ID NO: 1, 3, or 5 due to the degeneracy of the genetic code.

The phrase "a variant nucleotide sequence" can also mean, but is not limited to, a nucleotide sequence which hybridizes under stringent conditions with the nucleotide sequence complementary to the sequence shown in SEQ ID NO: 1, 3, 5, or a probe which can be prepared from the nucleotide sequence under stringent conditions provided that it encodes active or functional protein. "Stringent conditions" include those under which a specific hybrid, for example, a hybrid having homology, defined as the parameter "identity" when using the computer program BLAST, of not less than 50%, not less than 60%, not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1, 3, or 5 may also be used. Such a probe can be produced by PCR using oligonucleotides as primers prepared on the basis of the sequence shown in SEQ ID NO: 1, 3, or 5 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., 60° C. or 65° C.

As the genes encoding the FetB, FetA, and FieF proteins of the species *Escherichia coli* have already been elucidated (see above), a gene encoding an iron exporter, such as genes encoding the wild-type FetB, FetA, or FieF protein or variant proteins thereof, can be obtained by, for example, PCR (polymerase chain reaction; refer to White T. J. et al., The polymerase chain reaction, *Trends Genet.*, 1989, 5:185-189) from a microorganism harboring the wild-type fetB, fetA, and/or fieF genes, for example, a bacterium belonging to the family Enterobacteriaceae, utilizing primers prepared based on the nucleotide sequences of the fetB, fetA, and fieF genes; or the site-directed mutagenesis method by treating a DNA containing the wild-type fetB, fetA, and fieF genes in vitro, for example, with hydroxylamine, or a method for treating a microorganism harboring the wild-type fetB, fetA, and/or fieF genes, for example, a bacterium belonging to the family Enterobacteriaceae, with ultraviolet (UV) irradiation or a mutating agent such as N-methyl-N'-nitro-N-nitrosoguanidine (NTG) and nitrous acid usually used for the such treatment; or chemically synthesized as full-length gene structure. Genes encoding the FetB, FetA, and FieF proteins or variant proteins thereof from any other organism can be obtained in a similar manner.

The phrase "a wild-type protein" can mean a native protein naturally produced by an organism, specifically a wild-type or parent bacterial strain of the family Enterobacteriaceae, for example, by the wild-type *Escherichia coli* MG1655 strain. A wild-type protein can be encoded by the "wild-type gene", which can be present in genome of an organism, specifically a wild-type or parent bacterial strain.

The phrase "the fetB gene", "the fetA gene", or "the fieF gene" is not limited to the wild-type fetB, fetA, or fieF gene such as the fetB, fetA, or fieF gene shown in SEQ ID NO: 1, 3, or 5 and genes encoding the protein homologues of FetB, FetA and FieF shown in Tables 1-3, but can correctively refer to the wild-type fetB, fetA, or fieF gene and respective variant nucleotide sequences thereof.

The explanations given herein for variants of the genes and proteins regarding the iron exporter can also be applied mutatis mutandis to arbitrary genes and proteins, such as L-amino acid biosynthesis enzymes and genes encoding them.

The bacterium can have, in addition to the properties already mentioned, other specific properties such as various nutrient requirements, drug resistance, drug sensitivity, and drug dependence, without departing from the scope of the present invention.

2. Method

The method of the present invention includes a method for producing an L-amino acid. In the method, one kind of L-amino acid may be produced alone, or a mixture of two or more kinds of L-amino acids may be produced. The method for producing an L-amino acid can include the steps of cultivating the bacterium described above in a culture medium to allow the L-amino acid to be produced, excreted or secreted, and/or accumulated in the culture medium or in the bacterial cells, or both, and collecting the L-amino acid from the culture medium and/or the bacterial cells. The L-amino acid can be produced, for example, in a free form or as a salt thereof, or as a mixture thereof. That is, the phrase "L-amino acid" may refer to an L-amino acid in a free form, a salt form thereof, or a mixture thereof. For example, sodium, potassium, ammonium, and the like salts or an inner salt such as zwitterion of the L-amino acid can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to one skilled in the art. Also, L-amino acid can be produced in an adduct form thereof with, for example, another organic or inorganic compound. Specifically, a monochlorhydrate salt of an L-amino acid can be produced by the method such as monochlorhydrate salt of L-lysine (L-lysine×HCl) or monochlorhydrate salt of L-arginine (L-arginine×HCl).

The cultivation of the bacterium, and collection and purification of the L-amino acid from the medium and the like may be performed in a manner similar to conventional fermentation methods wherein an L-amino acid is produced using a microorganism. The culture medium to be used is not particularly limited, so long as the medium contains, at least, a carbon source, and the bacterium as described herein can proliferate in it and produce the L-amino acid. The culture medium for production of the L-amino acid can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. The medium can contain other various organic and inorganic components including, for example, vitamins such as vitamin B1, vitamin B2, vitamin B6, vitamin B12, nicotinic acid, and nicotinamide; required substances, for example, nucleic acids such as RNA, and amino acids; organic components containing these such as peptone, tryptone, casamino acid, yeast extract, and soybean protein decomposition product; and the like, which may be present in appropriate, even if trace, amounts. Other than these, small amounts of calcium phosphate, iron ions, manganese ions, and the like may be added, if necessary. As the other various organic and inorganic components, one kind of component may be used, or two or more kinds of components may be used in combination. Further, when an auxotrophic mutant strain that requires an amino acid or the like for growth thereof is used, it is preferable to supplement a required nutrient to the medium.

Cultivation can be performed under aerobic conditions for 16 to 72 h, or for 32 to 68 h; the culture temperature during cultivation can be controlled within 30 to 45° C., or within 30 to 37° C.; and the pH can be adjusted between 5 and 8, or between 6 and 7.5. The pH can be adjusted by using an inorganic or organic acidic or alkaline substance, as well as ammonia gas.

After cultivation, the target L-amino acid can be collected from the culture medium. Also, after cultivation, the target L-amino acid can be collected from the bacterial cells, specifically, the cells can be disrupted with, for example, supersonic waves or the like, a supernatant can be obtained by removing solids such as the cells and the cell-disrupted suspension (also referred to as cell debris) by, for example, centrifugation or membrane filtration, and then the target L-amino acid can be collected from the supernatant. Collection of the L-amino acid from the culture medium or the supernatant etc can be performed by any combination of conventional techniques such as concentration, crystallization, membrane treatment, ion-exchange chromatography, flash chromatography, thin-layer chromatography, high-performance liquid chromatography, and so forth. These methods may be independently used, or may be used in an appropriate combination.

The collected target L-amino acid composition may contain microbial cells, medium components, moisture, and by-product metabolites of the microorganism in addition to the target L-amino acid. Purity of the collected target L-amino acid can be 50% or higher, 85% or higher, or 95% or higher (U.S. Pat. No. 5,431,933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more specifically explained below with reference to the following non-limiting examples.

Example 1. Construction of the E. coli MG1655 Strains Having Modified Regulatory Regions of fieF and fetB Gene The fieF and fetB genes in *Escherichia coli* (*E. coli*) were overexpressed using the method developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, the PCR primer-pairs P1 (SEQ ID NO: 7)/P2 (SEQ ID NO: 8) for fieF and P3 (SEQ ID NO: 9)/P4 (SEQ ID NO: 10) for fetB, each of which is homologous to both a region adjacent to the corresponding gene and a region adjacent to the gene conferring kanamycin-resistance ($Km^R$, kan) or the Pnlp8φ10 promoter (SEQ ID NO: 11) in the template pMW-Km-Pnlp8 plasmid, were constructed. The pMW-Km-Pnlp8 plasmid (WO2014027702) was used as the template in PCR reaction. Conditions for PCR were as follows: denaturation for 3 min at 95° C.; profile for 25 cycles: 1 min at 95° C., 1 min at 57° C., 2 min at 72° C.; final elongation for 10 min at 72° C. The obtained DNA-fragment 1 (1951 bp, SEQ ID NO: 12) referred to as kan-Pnlp8φ10-fieF and DNA-fragment 2 (1951 bp, SEQ ID NO: 13) referred to as kan-Pnlp8φ10-fetB were purified in an agarose gel and used for electroporation of the strain *E. coli* MG1655 (ATCC 47076) containing the plasmid pKD46 with a temperature-sensitive replication origin. *E. coli* MG1655 strain is available from the American Type Culture Collection (P.O. Box 1549, Manassas, Va. 20108, United States of America). The plasmid pKD46 (Datsenko K. A. and Wanner B. L., *Proc. Natl. Acad. Sci. USA*, 2000, 97(12):6640-6645) includes a 2,154 nt (31088-33241) DNA-fragment of phage λ (GenBank, accession No. J02459) and contains genes of the λRed homologous recombination system (β, γ, and exo genes) under the control of arabinose-inducible $P_{araB}$ promoter. The plasmid pKD46 is necessary to integrate the DNA-fragments into the chromosome of *E. coli* MG1655 strain.

Electrocompetent cells were prepared as follows: *E. coli* MG1655 cells were grown overnight at 30° C. in LB-medium (Sambrook, J. and Russell, D. W. "Molecular Cloning: A Laboratory Manual", 3rd ed., Cold Spring Harbor Laboratory Press (2001)) containing ampicillin (100 mg/L), and the culture was diluted 100 times with 5 mL of SOB-medium (Sambrook J., Fritsch E. F. and Maniatis T., "Molecular Cloning: A Laboratory Manual", 2nd ed., Cold Spring Harbor Laboratory Press (1989)) containing ampicillin (100 mg/L) and L-arabinose (1 mM). The diluted culture was grown with aeration (250 rpm) at 30° C. to an $OD_{600}$ of about 0.6 and then made electrocompetent by concentrating 100-fold and washing three times with ice-cold deionized water. Electroporation was performed using 50 μL of cells and about 100 ng of the DNA-fragment 1 or DNA-fragment 2. Then, cells were incubated with 1 mL of SOC-medium (Sambrook J., Fritsch E. F. and Maniatis T., "Molecular Cloning: A Laboratory Manual", 2nd ed., Cold Spring Harbor Laboratory Press (1989)) at 37° C. for 2.5 h, placed onto the plates containing LB-medium, agar (1.5%) and kanamycin (20 mg/L), and grown at 37° C. to select $Km^R$-recombinants. To eliminate the pKD46 plasmid, one passage on L-agar with kanamycin (20 mg/L) at 42° C. was performed, and the obtained colonies were tested for sensitivity to ampicillin. Thus, the *E. coli* MG1655 kan-Pnlp8φ10-fieF and *E. coli* MG1655 kan-Pnlp8φ10-fetB strains were obtained.

The regulatory regions of fieF and fetB genes in the modified *E. coli* MG1655 kan-Pnlp8φ10-fieF and *E. coli* MG1655 kan-Pnlp8φ10-fetB strains were verified via the following procedure.

Cells containing the Pnlp8φ10-promoter regions of the fieF and fetB genes marked with $Km^R$-gene (kan) were verified by PCR using locus-specific primer-pairs P5 (SEQ ID NO: 14)/P6 (SEQ ID NO: 15) and P7 (SEQ ID NO: 16)/P8 (SEQ ID NO: 17), respectively, and the chromosome of the parent strain *E. coli* MG1655 as the control template. Conditions for PCR were as follows: denaturation for 2 min at 95° C.; profile for 25 cycles: 30 sec at 95° C., 30 sec at 57° C., 2 min at 72° C.; final elongation for 10 min at 72° C. As a result, the DNA-fragment 3 (333 bp, SEQ ID NO: 18) and DNA-fragment 4 (1036 bp, SEQ ID NO: 19) were obtained, respectively, from the control template. When chromosomes of the *E. coli* MG1655 kan-Pnlp8φ10-fieF and *E. coli* MG1655 kan-Pnlp8φ10-fetB strains were used as the templates, the DNA-fragment 5 (2145 bp, SEQ ID NO: 20) and DNA-fragment 6 (2148 bp, SEQ ID NO: 21) were obtained, respectively.

Example 2. Construction of E. coli L-Threonine-Producing Strain

The DNA-fragments 1 and 2 (Example 1) containing, respectively, the fieF and fetB genes under control of Pnlp8φ10 were each introduced into the L-threonine-producing *E. coli* B-3996Δtdh strain in the same manner as described in Example 1. The strain B-3996Δtdh was obtained by deleting the tdh gene on the chromosome of *E. coli* VKPM B-3996 (U.S. Pat. Nos. 5,175,107 and 5,705,371) using the "λRed/ET-mediated integration" method (Datsenko K. A. and Wanner B. L., *Proc. Natl. Acad. Sci. USA*, 2000, 97(12):6640-6645). The strain VKPM B-3996 was deposited on Nov. 19, 1987 in the All-Union Scientific Center of Antibiotics (Russian Federation, 117105 Moscow, Nagatinskaya Street, 3-A) under the accession number RIA 1867. The strain was also deposited in the Russian National Collection of Industrial Microorganisms (VKPM; FGUP GosNII Genetika, Russian Federation, 117545 Moscow, 1st Dorozhny proezd, 1) on Dec. 19, 2002 under the accession number VKPM B-3996.

Cells of the *E. coli* B-3996Δtdh that harbored the kan-Pnlp8φ10-fieF and kan-Pnlp8φ10-fetB cassettes were selected on the plates containing LB-medium, agar (1.5%) and kanamycin (20 mg/L). Thus, the L-threonine-producing *E. coli* B-3996Δtdh-kan-Pnlp8φ10-fieF and B-3996Δtdh-kan-Pnlp8φ10-fetB strains were obtained. The replacement of promoter regions of the fieF and fetB genes was verified using PCR as described above.

Example 3. Production of L-Threonine Using the Modified *E. coli* Strains

The modified *E. coli* B-3996Δtdh-kan-Pnlp8φ10-fieF and B-3996Δtdh-kan-Pnlp8φ10-fetB strains, and the control *E. coli* B-3996Δtdh strain were each cultivated at 32° C. for 18 hours in 20×200-mm test tubes containing 2 mL of L-broth supplemented with 4% (w/w) glucose. Then, 0.2 mL of the obtained cultures were each inoculated into 2 mL of a fermentation medium in 20×200-mm test tubes and cultivated at 32° C. for 65 hours on a rotary shaker at 250 rpm.

The composition of the fermentation medium (g/L) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4$—$7H_2O$ | 0.8 |
| $FeSO_4$—$7H_2O$ | 0.02 |
| $MnSO_4$—$5H_2O$ | 0.02 |
| Thiamine-HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. The antibiotic was introduced into the medium after sterilization.

After cultivation, the amount of L-threonine, which had accumulated in the medium, can be determined by paper chromatography using the following mobile phase: butanol-acetic acid-water=4:1:1 (v/v). A solution of ninhydrin (2%) in acetone was used as a visualizing reagent. After development, plates were dried and scanned with the Camag TLC Scanner 3 in absorbance mode with detection at 520 nm using winCATS software (version 1.4.2).

The results of five independent test tube fermentations of each strain are shown in Table 4. As it can be seen from the Table 4, the modified *E. coli* B-3996Δtdh-kan-Pnlp8φ10-fieF and *E. coli* B-3996Δtdh-kan-Pnlp8φ10-fetB strains were able to produce a higher amount of L-threonine as compared with the parent *E. coli* B-3996Δtdh strain.

TABLE 4

| Strain | Thr, g/L |
|---|---|
| *E. coli* B3996Δtdh | 19.3 |
| *E. coli* B3996Δtdh-kan-Pnlp8φ10-fieF | 20.5 |
| *E. coli* B3996Δtdh-kan-Pnlp8φ10-fetB | 20.1 |

Example 4. Production of L-Arginine Using the Modified *E. coli* Strains

To test the effect from overexpression of the fieF and fetB genes on L-arginine production, the DNA-fragments from the chromosomes of the above-described *E. coli* MG1655 kan-Pnlp8φ10-fieF and *E. coli* MG1655 kan-Pnlp8φ10-fetB strains are transferred to the arginine-producing *E. coli* strain 382 by P1-transduction to obtain the strains *E. coli* 382-kan-Pnlp8φ10-fieF and 382-kan-Pnlp8φ10-fetB. The strain 382 was deposited in the Russian National Collection of Industrial Microorganisms (VKPM; FGUP GosNII Genetika, Russian Federation, 117545 Moscow, 1st Dorozhny proezd, 1) on Apr. 10, 2000 under the accession number VKPM B-7926 and then converted to an international deposit under the provisions of the Budapest Treaty on May 18, 2001.

*E. coli* strains 382, 382-kan-Pnlp8φ10-fieF, and 382-kan-Pnlp8φ10-fetB are separately cultivated with shaking (220 rpm) at 37° C. for 18 hours in 3 mL of nutrient broth. Then, 0.3 mL of the obtained cultures are each inoculated into 2 mL of fermentation medium in 20×200-mm test tubes and cultivated at 32° C. for 48 hours on a rotary shaker (220 rpm).

After the cultivation, the amount of L-arginine which accumulates in the medium is determined by paper chromatography using a mobile phase consisting of n-butanol:acetic acid:water=4:1:1 (v/v). A solution of ninhydrin (2%) in acetone is used as a visualizing reagent. A spot containing L-arginine is cut out, L-arginine is eluted with 0.5% water solution of $CdCl_2$, and the amount of L-arginine is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4$—$7H_2O$ | 1.0 |
| Thiamine-HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 5. Production of L-Citrulline Using the Modified *E. coli* Strains

To test the effect from overexpression of the fieF and fetB genes on L-citrulline production, the DNA-fragments from the chromosomes of the above-described *E. coli* MG1655 kan-Pnlp8φ10-fieF and *E. coli* MG1655 kan-Pnlp8φ10-fetB strains are transferred to the citrulline-producing *E. coli* strain 382ΔargG by P1-transduction to obtain the strains *E. coli* 382ΔargG-kan-Pnlp8φ10-fieF and 382ΔargG-kan-Pnlp8φ10-fetB. The strain 382ΔargG is obtained by deletion of argG gene on the chromosome of the arginine-producing *E. coli* strain 382 (VKPM B-7926, EP1170358 A1) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, the PCR-primers, each of which is homologous to both a region adjacent to the argG gene and a region adjacent to the gene which confers antibiotic resistance in the template plasmid, are constructed. The plasmid pMW118-λattL-cat-λattR (WO05/010175) is used as the template in the PCR.

*E. coli* strains 382ΔargG, 382ΔargG-kan-Pnlp8φ10-fieF, and 382ΔargG-kan-Pnlp8φ10-fetB are separately cultivated with shaking at 37° C. for 18 hours in 3 mL of nutrient broth. Then, 0.3 mL of the obtained cultures are each inoculated into 2 mL of fermentation medium in 20×200-mm test tubes and cultivated at 32° C. for 48 hours on a rotary shaker.

After the cultivation, the amount of L-citrulline which accumulates in the medium is determined by paper chromatography using a mobile phase consisting of butan-1-ol:

acetic acid:water=4:1:1 (v/v). A solution of ninhydrin (2%) in acetone is used as a visualizing reagent. A spot containing citrulline is cut out, L-citrulline is eluted with 0.5% water solution of $CdCl_2$, and the amount of L-citrulline is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4$—$7H_2O$ | 1.0 |
| Thiamine-HCl | 0.0002 |
| Yeast extract | 1.0 |
| L-Isoleucine | 0.1 |
| L-Arginine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 6. Production of L-Cysteine Using the Modified E. coli Strains

To test the effect from overexpression of the fieF and fetB genes on L-cysteine production, the DNA-fragments from the chromosomes of the above-described E. coli MG1655 kan-Pnlp8φ10-fieF and E. coli MG1655 kan-Pnlp8φ10-fetB strains are transferred to the cysteine-producing E. coli strain JM15(ydeD) by P1-transduction to obtain the strains E. coli JM15(ydeD)-kan-Pnlp8φ10-fieF and JM15(ydeD)-kan-Pnlp8φ10-fetB. The strain JM15(ydeD) is a derivative of E. coli JM15 (U.S. Pat. No. 6,218,168 B1), which is transformed with DNA containing the ydeD gene (U.S. Pat. No. 5,972,663). E. coli JM15 strain (CGSC#5042) is available from the E. coli Genetic Stock Center (Yale University, New Haven, USA). The ydeD gene encodes a membrane protein, and it is not involved in a biosynthetic pathway of any L-amino acid.

Fermentation conditions and procedure for evaluation of L-cysteine production were described in detail in Example 6 of U.S. Pat. No. 6,218,168 B1.

Example 7. Production of L-Glutamic Acid Using the Modified E. coli Strains

To test the effect from overexpression of the fieF and fetB genes on L-glutamic acid production, the DNA-fragments from the chromosomes of the above-described E. coli MG1655 kan-Pnlp8φ10-fieF and E. coli MG1655 kan-Pnlp8φ10-fetB strains are transferred to the glutamate-producing E. coli strain VL334thrC$^+$ (EP1172433 A1) by P1-transduction to obtain the strains E. coli VL334thrC$^+$-kan-Pnlp8φ10-fieF and VL334thrC$^+$-kan-Pnlp8φ10-fetB. The strain VL334thrC$^+$ was deposited in the Russian National Collection of Industrial Microorganisms (VKPM; FGUP GosNII Genetika, Russian Federation, 117545 Moscow, 1 Dorozhny proezd, 1) on Dec. 6, 2004 under the accession number VKPM B-8961 and then converted to an international deposit under the provisions of the Budapest Treaty on Dec. 8, 2004.

E. coli strains VL334thrC$^+$, VL334thrC$^+$-kan-Pnlp8φ10-fieF, and VL334thrC$^+$-kan-Pnlp8φ10-fetB are separately cultivated for 18-24 hours at 37° C. on L-agar plates. Then, one loop of the cells is transferred into 20×200-mm test tubes containing 2 mL of fermentation medium. Cultivation is carried out at 30° C. for 3 days with shaking.

After the cultivation, the amount of L-glutamic acid which accumulates in the medium is determined by paper chromatography using a mobile phase consisting of butan-1-ol:acetic acid:water=4:1:1 (v/v) with subsequent staining by ninhydrin (1% solution in acetone), elution of L-glutamic acid in 50% ethanol with 0.5% $CdCl_2$ and further estimation of the amount of L-glutamic acid at 540 nm.

The composition of the fermentation medium (g/L) is as follows:

| | |
|---|---|
| Glucose | 60.0 |
| $(NH_4)_2SO_4$ | 25.0 |
| $KH_2PO_4$ | 2.0 |
| $MgSO_4$—$7H_2O$ | 1.0 |
| Thiamine-HCl | 0.1 |
| L-Isoleucine | 0.07 |
| $CaCO_3$ | 25.0 |

Glucose and $CaCO_3$ are sterilized separately. The pH is adjusted to 7.2.

Example 8. Production of L-Histidine Using the Modified E. coli Strains

To test the effect from overexpression of the fieF and fetB genes on L-histidine production, the DNA-fragments from the chromosomes of the above-described E. coli MG1655 kan-Pnlp8φ10-fieF and E. coli MG1655 kan-Pnlp8φ10-fetB strains are transferred to the L-histidine-producing E. coli strain 80 using the P1-transduction to obtain the strains E. coli 80-kan-Pnlp8φ10-fieF and 80-kan-Pnlp8φ10-fetB. The strain 80 was described in Russian Patent No. 2119536 C1 and deposited in the Russian National Collection of Industrial Microorganisms (VKPM; FGUP GosNII Genetika, Russian Federation, 117545 Moscow, 1 Dorozhny proezd, 1) on Oct. 15, 1999 under the accession number VKPM B-7270 and then converted to an international deposit under the provisions of the Budapest Treaty on Jul. 12, 2004.

E. coli strains 80, 80-kan-Pnlp8φ10-fieF, and 80-kan-Pnlp8φ10-fetB are separately cultivated for 6 hours at 29° C. in 2 mL of L-broth (Sambrook J. and Russell D. W., Molecular Cloning: A Laboratory Manual (3$^{rd}$ ed.), Cold Spring Harbor Laboratory Press, 2001). Then, 0.1 mL of the obtained cultures are each inoculated into 2 mL of fermentation medium in 20×200-mm test tubes and cultivated for 65 hours at 29° C. on a rotary shaker (350 rpm).

The composition of the fermentation medium (g/L) is as follows:

| | |
|---|---|
| Glucose | 100.0 |
| Mameno* | 0.2 |
| | (as the amount of nitrogen) |
| L-proline | 1.0 |
| $(NH_4)_2SO_4$ | 25.0 |
| $KH_2PO_4$ | 2.0 |
| $MgSO_4$—$7H_2O$ | 1.0 |
| $FeSO_4$—$7H_2O$ | 0.01 |
| $MnSO_4$—$5H_2O$ | 0.02 |
| Thiamine-HCl | 0.001 |
| Betaine | 2.0 |
| $CaCO_3$ | 60.0 |

*Mameno is the soybean meal hydrolysate (Ajinomoto Co., Inc.).

Glucose, magnesium sulphate, betaine, and $CaCO_3$ are sterilized separately. The pH is adjusted to 6.0 by 6M KOH solution before sterilization.

After the cultivation, the amount of L-histidine which accumulates in the medium is determined by thin layer chromatography (TLC). The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:acetone:25% aqueous ammonia:water=6:6:1.5:1 (v/v). A solution of ninhydrin (2%, w/v) in acetone is used as a visualizing reagent. After development, plates are dried and scanned with the Camag TLC Scanner 3 in absorbance mode with detection at 520 nm using winCATS software (version 1.4.2).

Example 9. Production of L-Leucine Using the Modified *E. coli* Strains

To test the effect from overexpression of the fieF and fetB genes on L-leucine production, the DNA-fragments from the chromosomes of the above-described *E. coli* MG1655 kan-Pnlp8φ10-fieF and *E. coli* MG1655 kan-Pnlp8φ10-fetB strains are transferred to the leucine-producing *E. coli* strain 57 (VKPM B-7386, U.S. Pat. No. 6,124,121) by P1-transduction to obtain the strains *E. coli* 57-kan-Pnlp8φ10-fieF and 57-kan-Pnlp8φ10-fetB. The strain 57 was deposited in the Russian National Collection of Industrial Microorganisms (VKPM; FGUP GosNII Genetika, Russian Federation, 117545 Moscow, 1st Dorozhny proezd, 1) on May 19, 1997 under the accession number VKPM B-7386.

*E. coli* strains 57, 57-kan-Pnlp8φ10-fieF, and 57-kan-Pnlp8φ10-fetB are separately cultivated for 18-24 hours at 37° C. on L-agar plates. To obtain a seed culture, the strains are each grown on a rotary shaker (250 rpm) at 32° C. for 18 hours in 20×200-mm test tubes containing 2 mL of L-broth (Sambrook J. and Russell D. W., Molecular Cloning: A Laboratory Manual (3$^{rd}$ ed.), Cold Spring Harbor Laboratory Press, 2001) supplemented with sucrose (4%). Then, the fermentation medium is inoculated with 0.2 mL of seed material (10%). The fermentation is performed in 2 mL of a minimal fermentation medium in 20×200-mm test tubes. Cells are grown for 48-72 hours at 32° C. with shaking at 250 rpm.

After the cultivation, the amount of L-leucine which accumulates in the medium is determined by paper chromatography using a mobile phase consisting of butan-1-ol:acetic acid:water=4:1:1 (v/v).

The composition of the fermentation medium (g/L) is as follows:

| | |
|---|---|
| Glucose | 60.0 |
| (NH$_4$)$_2$SO$_4$ | 25.0 |
| K$_2$HPO$_4$ | 2.0 |
| MgSO$_4$—7H$_2$O | 1.0 |
| Thiamine-HCl | 0.01 |
| CaCO$_3$ | 25.0 |

Glucose is sterilized separately. CaCO$_3$ is dry-heat sterilized at 180° C. for 2 h. The pH is adjusted to 7.2.

Example 10. Production of L-Lysine Using the Modified *E. coli* Strains

To test the effect from overexpression of the fieF and fetB genes on L-lysine production, the DNA-fragments from the chromosomes of the above-described *E. coli* MG1655 kan-Pnlp8φ10-fieF and *E. coli* MG1655 kan-Pnlp8φ10-fetB strains are transferred to the lysine-producing *E. coli* strain AJ11442 by P1-transduction to obtain the strains *E. coli* AJ11442-kan-Pnlp8φ10-fieF and AJ11442-kan-Pnlp8φ10-fetB. The strain AJ11442 was deposited in Fermentation Research Institute, Agency of Industrial Science and Technology (currently, NITE IPOD, #120, 2-5-8 Kazusakamatari, Kisarazu-shi, Chiba, 292-0818, Japan) on May 1, 1981 under the deposition number FERM P-5084 and received an accession number of FERM BP-1543. The pCABD2 plasmid includes the dapA gene encoding dihydrodipicolinate synthase having a mutation which desensitizes feedback inhibition by L-lysine, the lysC gene encoding aspartokinase III having a mutation which desensitizes feedback inhibition by L-lysine, the dapB gene encoding dihydrodipicolinate reductase, and the ddh gene encoding diaminopimelate dehydrogenase (U.S. Pat. No. 6,040,160).

*E. coli* strains AJ11442, AJ11442-kan-Pnlp8φ10-fieF, and AJ11442-kan-Pnlp8φ10-fetB are separately cultivated in L-medium containing streptomycin (20 mg/L) at 37° C. Then, 0.3 mL of the obtained cultures are each inoculated into 20 mL of fermentation medium containing the required drugs in a 500-mL flask. The cultivation is carried out at 37° C. for 16 hours by using a reciprocal shaker at the agitation speed of 115 rpm.

After the cultivation, the amount of L-lysine which accumulates in the medium and residual glucose are determined by a known method (Biotech-analyzer AS210, Sakura Seiki Co.). Then, the yield of L-lysine is calculated relative to consumed glucose for each of the strains.

The composition of the fermentation medium (g/L) is as follows:

| | |
|---|---|
| Glucose | 40.0 |
| (NH$_4$)$_2$SO$_4$ | 24.0 |
| K$_2$HPO$_4$ | 1.0 |
| MgSO$_4$—7H$_2$O | 1.0 |
| FeSO$_4$—7H$_2$O | 0.01 |
| MnSO$_4$—5H$_2$O | 0.01 |
| Yeast extract | 2.0 |

The pH is adjusted to 7.0 by KOH, and the medium is autoclaved at 115° C. for 10 min. Glucose and magnesium sulfate are sterilized separately. CaCO$_3$ is dry-heat sterilized at 180° C. for 2 hours and added to the medium to a final concentration of 30 g/L.

Example 11. Production of L-Ornithine Using the Modified *E. coli* Strains

To test the effect from overexpression of the fieF and fetB genes on L-ornithine production, the DNA-fragments from the chromosomes of the above-described *E. coli* MG1655 kan-Pnlp8φ10-fieF and *E. coli* MG1655 kan-Pnlp8φ10-fetB strains are transferred to the ornithine-producing *E. coli* strain 382ΔargFΔargI by P1-transduction to obtain the strains *E. coli* 382ΔargFΔargI-kan-Pnlp8φ10-fieF and 382ΔargFΔargI-kan-Pnlp8φ10-fetB. The strain 382ΔargFΔargI is obtained by consecutive deletion of argF and argI genes on the chromosome of the arginine-producing *E. coli* strain 382 (VKPM B-7926, EP1170358 A1) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, two pairs of PCR-primers homologous to both the region adjacent to the argF or argI gene and the gene which confers antibiotic resistance in the template plasmid are constructed. The plasmid pMW118-λattL-cat-λattR (WO05/010175) is used as the template in the PCR.

E. coli strains 382ΔargFΔargI, 382ΔargFΔargI-kan-Pnlp8φ10-fieF, and 382ΔargFΔargI-kan-Pnlp8φ10-fetB are separately cultivated with shaking at 37° C. for 18 hours in 3 mL of nutrient broth. Then, 0.3 mL of the obtained cultures are each inoculated into 2 mL of fermentation medium in 20×200-mm test tubes and cultivated at 32° C. for 48 hours on a rotary shaker.

After the cultivation, the amount of L-ornithine which accumulates in the medium is determined by paper chromatography using a mobile phase consisting of butan-1-ol:acetic acid:water=4:1:1 (v/v). A solution of ninhydrin (2%) in acetone is used as a visualizing reagent. A spot containing ornithine is cut out, ornithine is eluted with 0.5% water solution of $CdCl_2$, and the amount of ornithine is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4-7H_2O$ | 1.0 |
| Thiamine-HCl | 0.0002 |
| Yeast extract | 1.0 |
| L-Isoleucine | 0.1 |
| L-Arginine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 12. Production of L-Phenylalanine Using the Modified E. coli Strains To test the effect from overexpression of the fieF and fetB genes on L-phenylalanine production, the DNA-fragments from the chromosomes of the above-described E. coli MG1655 kan-Pnlp8φ10-fieF and E. coli MG1655 kan-Pnlp8φ10-fetB strains are transferred to the phenylalanine-producing E. coli strain AJ12739 by P1-transduction to obtain the strains E. coli AJ12739-kan-Pnlp8φ10-fieF and AJ12739-kan-Pnlp8φ10-fetB. The strain AJ12739 was deposited in the Russian National Collection of Industrial Microorganisms (VKPM; FGUP GosNII Genetika, Russian Federation, 117545 Moscow, 1st Dorozhny proezd, 1) on Nov. 6, 2001 under the accession number VKPM B-8197 and then converted to an international deposit under the provisions of the Budapest Treaty on Aug. 23, 2002.

E. coli strains AJ12739, AJ12739-kan-Pnlp8φ10-fieF, and AJ12739-kan-Pnlp8φ10-fetB are separately cultivated at 37° C. for 18 hours in a nutrient broth. Then, 0.3 mL of the obtained cultures are each inoculated into 3 mL of fermentation medium in 20 to 3 mL of fermentation medium in 20×200-mm test tubes and cultivated at 37° C. for 48 hours with shaking on a rotary shaker.

After the cultivation, the amount of L-phenylalanine which accumulates in the medium is determined by thin layer chromatography (TLC). The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethyl acetate:25% aqueous ammonia:water=40:40:7:16 (v/v). A solution of ninhydrin (2%) in acetone is used as a visualizing reagent.

The composition of the fermentation medium (g/L) is as follows:

| | |
|---|---|
| Glucose | 40.0 |
| $(NH_4)_2SO_4$ | 16.0 |
| $K_2HPO_4$ | 0.1 |
| $MgSO_4-7H_2O$ | 1.0 |
| $FeSO_4-7H_2O$ | 0.01 |
| $MnSO_4-5H_2O$ | 0.01 |
| Thiamine-HCl | 0.0002 |
| Yeast extract | 2.0 |
| L-Tyrosine | 0.125 |
| $CaCO_3$ | 20.0 |

Glucose and magnesium sulfate are sterilized separately. $CaCO_3$ is dry-heat sterilized at 180° C. for 2 h. The pH is adjusted to 7.0.

Example 13. Production of L-Proline Using the Modified E. coli Strains

To test the effect from overexpression of the fieF and fetB genes on L-proline production, the DNA-fragments from the chromosomes of the above-described E. coli MG1655 kan-Pnlp8φ10-fieF and E. coli MG1655 kan-Pnlp8φ10-fetB strains are transferred to the proline-producing E. coli strain 702ilvA by P1-transduction to obtain the strains E. coli 702ilvA-kan-Pnlp8φ10-fieF and 702ilvA-kan-Pnlp8φ10-fetB. The strain 702ilvA was deposited in the Russian National Collection of Industrial Microorganisms (VKPM; FGUP GosNII Genetika, Russian Federation, 117545 Moscow, 1st Dorozhny proezd, 1) on Jul. 18, 2000 under the accession number VKPM B-8012 and then converted to an international deposit under the provisions of the Budapest Treaty on May 18, 2001.

E. coli strains 702ilvA, 702ilvA-kan-Pnlp8φ10-fieF, and 702ilvA-kan-Pnlp8φ10-fetB are separately cultivated for 18-24 hours at 37° C. on L-agar plates. Then, these strains are each cultivated under the same conditions as in Example 7 (production of L-glutamic acid).

Example 14. Production of L-Tryptophan Using the Modified E. coli Strains

To test the effect from overexpression of the fieF and fetB genes on L-tryptophan production, the DNA-fragments from the chromosomes of the above-described E. coli MG1655 kan-Pnlp8φ10-fieF and E. coli MG1655 kan-Pnlp8φ10-fetB strains are transferred to the tryptophan-producing E. coli strain SV164(pGH5) by P1-transduction to obtain the strains E. coli SV164(pGH5)-kan-Pnlp8φ10-fieF and SV164(pGH5)-kan-Pnlp8φ10-fetB. The strain SV164(pGH5) is a strain obtained by introducing the plasmid pGH5 into the E. coli strain SV164. The strain SV164 (JP 3032013 B) has the trpE allele encoding anthranilate synthase free from feedback inhibition by tryptophan. The strain SV164 is a strain obtained by introducing a mutation into the trpE gene in the E. coli strain YMC9 (ATCC 33927). The strain YMC9 is available from the American Type Culture Collection (P.O. Box 1549, Manassas, Va. 20108, United States of America). The plasmid pGH5 harbors a mutant serA gene encoding phosphoglycerate dehydrogenase free from feedback inhibition by serine. The strain SV164(pGH5) was described in detail in U.S. Pat. No. 6,180,373 B1 or EP0662143 B1.

E. coli strains SV164(pGH5), SV164(pGH5)-kan-Pnlp8φ10-fieF, and SV164(pGH5)-kan-Pnlp8φ10-fetB are separately cultivated with shaking at 37° C. for 18 hours in 3 mL of nutrient broth supplemented with tetracycline (20 mg/L, marker of pGH5 plasmid). Then, 0.3 mL of the obtained cultures are each inoculated into 3 mL of a fermentation medium containing tetracycline (20 mg/L) in 20×200-mm test tubes, and cultivated at 37° C. for 48 hours on a rotary shaker at 250 rpm.

After the cultivation, the amount of L-tryptophan which accumulates in the medium is determined by TLC as described in Example 12 (production of L-phenylalanine). The fermentation medium components are listed in Table 5, but should be sterilized in separate groups (A, B, C, D, E, F, G, and H), as shown, to avoid adverse interactions during sterilization.

TABLE 5

| Solutions | Component | Final concentration, g/L |
|---|---|---|
| A | $KH_2PO_4$ | 1.5 |
|   | NaCl | 0.5 |
|   | $(NH_4)_2SO_4$ | 1.5 |
|   | L-Methionine | 0.05 |
|   | L-Phenylalanine | 0.1 |
|   | L-Tyrosine | 0.1 |
|   | Mameno* (as the amount of nitrogen) | 0.07 |
| B | Glucose | 40.0 |
|   | $MgSO_4 \cdot 7H_2O$ | 0.3 |
| C | $CaCl_2$ | 0.011 |
| D | $FeSO_4 \cdot 7H_2O$ | 0.075 |
|   | Sodium citrate | 1.0 |
| E | $Na_2MoO_4 \cdot 2H_2O$ | 0.00015 |
|   | $H_3BO_3$ | 0.0025 |
|   | $CoCl_2 \cdot 6H_2O$ | 0.00007 |
|   | $CuSO_4 \cdot 5H_2O$ | 0.00025 |
|   | $MnCl_2 \cdot 4H_2O$ | 0.0016 |
|   | $ZnSO_4 \cdot 7H_2O$ | 0.0003 |
| F | Thiamine-HCl | 0.005 |
| G | $CaCO_3$ | 30.0 |
| H | Pyridoxine | 0.03 |

The pH of solution A is adjusted to 7.1 with $NH_4OH$.
*Mameno is the soybean meal hydrolysate (Ajinomoto Co., Inc.).

Example 15. Production of L-Valine Using the Modified E. coli Strains

To test the effect from overexpression of the fieF and fetB genes on L-valine production, the DNA fragments from the chromosomes of the above-described E. coli MG1655 kan-Pnlp8φ10-fieF and E. coli MG1655 kan-Pnlp8φ10-fetB strains are transferred to the valine-producing E. coli strain H81 by P1-transduction to obtain the strains E. coli H81-kan-Pnlp8φ10-fieF and H81-kan-Pnlp8φ10-fetB. The strain H81 was deposited in the Russian National Collection of Industrial Microorganisms (VKPM; FGUP GosNII Genetika, Russian Federation, 117545 Moscow, 1st Dorozhny Proezd, 1) on Jan. 30, 2001 under accession number VKPM B-8066, and converted to international deposit under the Budapest Treaty on Feb. 1, 2002.

E. coli strains H81, H81-kan-Pnlp8φ10-fieF, and H81-kan-Pnlp8φ10-fetB are separately cultivated at 37° C. for 18 h in a nutrient broth. The obtained cultures (0.1 mL each) are inoculated into 2 mL of a fermentation medium in a 20×200-mm test tubes, and cultivated at 32° C. for 72 h with a rotary shaker at 250 rpm.

After the cultivation, the amount of L-valine which accumulates in the medium is measured by TLC. The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethyl acetate:25% aqueous ammonia:water=40:40:7:16 (v/v). A solution of ninhydrin (2%) in acetone is used as a visualizing reagent.

Fermentation Medium Composition (g/L):

| | |
|---|---|
| Glucose | 60.0 |
| $(NH_4)_2SO_4$ | 15.0 |
| $KH_2PO_4$ | 1.5 |
| $MgSO_4$—$7H_2O$ | 1.0 |
| Mameno | 0.4 |
|  | (as the amount of nitrogen) |
| $CaCO_3$ | 25.0 |

$CaCO_3$ is dry-heat sterilized at 180° C. for 2 h. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-amino acids by fermentation of a bacterium of the family Enterobacteriaceae having an L-amino acid-producing ability can be improved, and thereby the L-amino acids can be efficiently produced by the bacterium.

The invention claimed is:

1. A method for producing an L-amino acid comprising:
 (i) cultivating an L-amino acid-producing bacterium of the family Enterobacteriaceae in a culture medium to produce and accumulate the L-amino acid in the culture medium, and
 (ii) collecting the L-amino acid from the culture medium,
 wherein said bacterium has been modified to overexpress a gene encoding an iron exporter compared to expression of said gene in the corresponding unmodified bacterium,
 wherein said gene encoding an iron exporter is overexpressed by increasing the copy number of said gene, and/or modifying an expression regulatory region of said gene, so that the expression of said gene is enhanced as compared with the corresponding unmodified bacterium,
 wherein said gene encoding an iron exporter encodes a protein selected from the group consisting of:
 (A) a protein comprising the amino acid sequence of SEQ ID NO: 2, 4 or 6;
 (B) a protein comprising the amino acid sequence of SEQ ID NO: 2, 4 or 6, but which includes substitution, deletion, insertion, and/or addition of one to ten amino acid residues, wherein said protein has an iron exporter activity; and
 (C) a protein comprising an amino acid sequence that is not less than 95% identical to the entire amino acid sequence of SEQ ID NO: 2, 4 or 6, wherein said protein has an iron exporter activity.

2. The method according to claim 1, wherein said gene encoding an iron exporter is a DNA selected from the group consisting of:

(A) a DNA comprising the nucleotide sequence of SEQ ID NO: 1, 3 or 5;
(B) a DNA encoding a protein comprising the amino acid sequence of SEQ ID NO: 2, 4 or 6, but which includes substitution, deletion, insertion and/or addition of one to ten amino acid residues, wherein said protein has an iron exporter activity; and
(C) a DNA comprising a variant nucleotide sequence of SEQ ID NO: 1, 3, or 5, wherein said DNA encodes the protein of SEQ ID NOs: 2, 4, or 6, respectively.

3. The method according to claim 1, wherein said bacterium belongs to the genus *Escherichia*.

4. The method according to claim 3, wherein said bacterium is *Escherichia coli*.

5. The method according to claim 1, wherein said bacterium belongs to the genus *Pantoea*.

6. The method according to claim 5, wherein said bacterium is *Pantoea ananatis*.

7. The method according to claim 1, wherein said L-amino acid is an L-amino acid belonging to the aspartate family.

8. The method according to claim 7, wherein said L-amino acid belonging to the aspartate family is selected from the group consisting of L-asparagine, L-aspartic acid, L-isoleucine, L-lysine, L-methionine, and L-threonine.

* * * * *